(12) United States Patent
Barawkar et al.

(10) Patent No.: US 8,940,751 B2
(45) Date of Patent: Jan. 27, 2015

(54) PURINE COMPOUNDS AS PRODRUGS OF A2B ADENOSINE RECEPTOR ANTAGONISTS, THEIR PROCESS AND MEDICINAL APPLICATIONS

(75) Inventors: Dinesh Barawkar, Pune (IN); Sujay Basu, Pune (IN); Vidya Ramdas, Pune (IN); Venkata Poornapragnacharyulu Palle, Pune (IN); Yogesh Waman, Pune (IN); Meena Patel, Pune (IN); Anil Panmand, Pune (IN)

(73) Assignee: Advinus Therapeutics Private Limited, Bangalore (IN)

( * ) Notice: Subject to any disclaimer, the term of this patent is extended or adjusted under 35 U.S.C. 154(b) by 0 days.

(21) Appl. No.: 13/821,481

(22) PCT Filed: Sep. 9, 2011

(86) PCT No.: PCT/IN2011/000620
§ 371 (c)(1),
(2), (4) Date: Mar. 7, 2013

(87) PCT Pub. No.: WO2012/035548
PCT Pub. Date: Mar. 22, 2012

(65) Prior Publication Data
US 2013/0172249 A1    Jul. 4, 2013

(30) Foreign Application Priority Data

Sep. 13, 2010    (IN) .......................... 2671/CHE/2010

(51) Int. Cl.
| | | |
|---|---|---|
| A61K 31/522 | (2006.01) | |
| C07D 473/30 | (2006.01) | |
| C07F 9/6561 | (2006.01) | |
| A61K 31/675 | (2006.01) | |
| A61K 45/06 | (2006.01) | |

(52) U.S. Cl.
CPC ............ *A61K 31/522* (2013.01); *C07D 473/30* (2013.01); *C07F 9/65616* (2013.01); *A61K 31/675* (2013.01); *A61K 45/06* (2013.01)
USPC ..................... 514/263.1; 514/263.2; 514/161; 544/264; 544/276

(58) Field of Classification Search
CPC ... A61K 31/522; A61K 31/675; A61K 45/06; C07D 473/30; C07F 9/65616
See application file for complete search history.

(56) References Cited

U.S. PATENT DOCUMENTS

| | | | | |
|---|---|---|---|---|
| 2,628,235 A | * | 2/1953 | Hitchings et al. ............. | 544/276 |
| 6,579,868 B1 | | 6/2003 | Asano et al. | |
| 6,825,349 B2 | * | 11/2004 | Kalla et al. .................... | 544/267 |
| 6,977,300 B2 | * | 12/2005 | Kalla et al. .................... | 544/269 |
| 7,304,070 B2 | * | 12/2007 | Kalla et al. ................. | 514/263.2 |
| 7,625,881 B2 | | 12/2009 | Kalla et al. | |
| 7,741,331 B2 | * | 6/2010 | Kalla et al. ................. | 514/263.2 |
| 8,324,224 B2 | * | 12/2012 | Kalla et al. ................. | 514/263.2 |
| 2002/0198205 A1 | * | 12/2002 | Himmelsbach et al. ... | 514/234.5 |
| 2003/0229106 A1 | * | 12/2003 | Kalla et al. ................. | 514/263.2 |
| 2005/0004149 A1 | | 1/2005 | Harada et al. | |
| 2005/0119287 A1 | | 6/2005 | Kalla et al. | |
| 2006/0264432 A1 | | 11/2006 | Rosentreter et al. | |
| 2006/0281927 A1 | | 12/2006 | Tomisawa et al. | |
| 2007/0219178 A1 | * | 9/2007 | Muramoto ............... | 514/210.21 |
| 2009/0018331 A1 | * | 1/2009 | Yoshikawa et al. ............ | 544/95 |
| 2012/0115864 A1 | | 5/2012 | Palle et al. | |

FOREIGN PATENT DOCUMENTS

| | | |
|---|---|---|
| EP | 1283056 | 2/2003 |
| WO | 0073307 | 12/2000 |

(Continued)

OTHER PUBLICATIONS

McLaughlin et al., J. Phys. Chem. A (2006), vol. 110:6224-6230.*

(Continued)

*Primary Examiner* — Christina Bradley
*Assistant Examiner* — Randall L Beane
(74) *Attorney, Agent, or Firm* — Perkins Coie LLP

(57) ABSTRACT

The present disclosure relates to purine compounds of formula (I) or formula (II) or its tautomers, polymorphs, stereoisomers, solvates or a pharmaceutically acceptable salts, or pharmaceutical compositions containing them and methods of treating conditions and diseases that are mediated by thereof as A2B adenosine receptor antagonists.

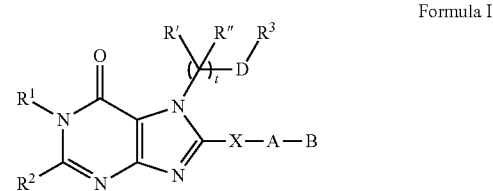

Formula I

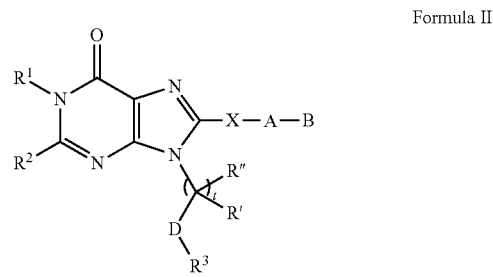

Formula II

The compounds of the present disclosure are useful in the treatment, prevention or suppression of diseases and disorders that may be susceptible to improvement by the mediation of adenosine A2B receptor. The present disclosure also relates to methods for the preparation of such compounds, and to pharmaceutical compositions containing them.

5 Claims, No Drawings

(56) References Cited

FOREIGN PATENT DOCUMENTS

| | | |
|---|---|---|
| WO | 03000694 | 1/2003 |
| WO | 03002566 | 1/2003 |
| WO | 03006465 | 1/2003 |
| WO | 03042214 | 5/2003 |
| WO | 03053361 | 7/2003 |
| WO | 03063800 | 8/2003 |
| WO | 03082873 | 10/2003 |
| WO | 2004106337 | 12/2004 |
| WO | 2005021548 | 3/2005 |
| WO | 2005042534 | 5/2005 |
| WO | 2006015357 | 2/2006 |
| WO | 2006091896 | 8/2006 |
| WO | 2007017096 | 2/2007 |
| WO | 2007109547 | 9/2007 |
| WO | 2007149277 | 12/2007 |
| WO | 2008002902 | 1/2008 |

OTHER PUBLICATIONS

Zhang et al., "Detrimental effects of adenosine signaling in sickle cell disease", Nature Medicine, vol. 17, No. 1, Jan. 2011, pp. 79-87.

* cited by examiner

PURINE COMPOUNDS AS PRODRUGS OF A2B ADENOSINE RECEPTOR ANTAGONISTS, THEIR PROCESS AND MEDICINAL APPLICATIONS

TECHNICAL FIELD

PRIORITY CLAIM

This is a national stage application of PCT Application No. PCT/IN2011/000620, filed on Sep. 9, 2011, which claims priority to India Patent Application No. 2671/CHE/2010, filed on Sep. 13, 2010, the entire contents of each of which are incorporated by reference in their entireties.

The present disclosure relates to parine compounds or its tautomers, polymorphs, stereoisomers, solvates or pharmaceutically acceptable salts thereof, as prodrugs of $A_{2B}$ adenosine receptor antagonists, and to their use in treating mammals for various disease states, such as gastrointestinal disorders, immunological disorders, hypersensitivity disorders, neurological disorders, and cardiovascular diseases due to both cellular hyperproliferation and apoptosis, and the like. The disclosure also relates to methods for the preparation of such compounds, and to pharmaceutical compositions containing them.

BACKGROUND

Adenosine is known to be an endogenous modulator of a number of physiological functions and these are mediated by the interaction with different membrane specific receptors which belong to the family of receptors coupled with G proteins. Adenosine exerts effects in cardiovascular, central nervous, respiratory systems, kidney, adipose and platelets. Recent advances in molecular biolog) coupled with several pharmacological studies have lead to identification of at least four subtypes of adenosine receptors, $A_1$, $A_{2B}$, $A_{2b}$ and $A_3$. The $A_1$ and $A_3$ receptors down-regulate cellular cAMP levels through their coupling to G protein, which inhibit adenylate cyclase. In contrast, $A_{2A}$ and $A_{2B}$ receptors couple to G protein that activate adenylate cyclase and increase intracellular levels of cAMP.

Advances in understanding the role of adenosine and its receptors in physiology and pathophysiology as well as new developments in medicinal chemistry of these receptors have identified potential therapeutic areas for drug development. With the combination of pharmacological data, using selective ligands and genetically modified mice, important progress has been made toward an understanding of the role of ARs in a variety of diseases, such as inflammatory conditions, sepsis, heart attack, ischemia-reperfusion injury, vascular injury, spinal cord injury, chronic obstructive pulmonary disease (COPD), asthma, diabetes, obesity, inflammatory bowel disease, retinopathy, and Parkinson's Disease (PD).

The $A_{2B}$ adenosine receptor subtype (see Fektistov, I., Biaggioni, I. Pharmacol. Rev. 1997, 49, 381-402) has been identified in a variety of human and murine tissues and is involved in the regulation of vascular tone, smooth muscle growth, angiogenesis, hepatic glucose production, bowel movement, intestinal secretion, and mast cell degranulation. $A_{2B}$ receptors have been implicated in mast cell activation and asthma, control of vascular tone, cardiac myocyte contractility, cell growth and gene expression, vasodilation, regulation of cell growth, intestinal function, and modulation of neurosecretion (Pharmacological Reviews Vol. 49, No. 4).

$A_{2B}$ receptors modulate mast cell function. Adenosine activates adenylate cyclase and protein kinase C, and potentiates stimulated mediator release in mouse bone marrow derived mast cells. (TiPS—April 1998 (Vol. 19)). Activation of $A_{2B}$ receptors in HMC-1 augments IL-8 release and potentiates PMA-induced secretion of IL-8. Thus, adenosine would contribute to the asthmatic response by acting on the mast cell to enhance the release of proinflammatory mediators. (Pulmonary Pharmacology & Therapeutics 1999, 12, 111-114). In COPD, transformation of pulmonary fibroblasts into myofibroblasts is considered a major mechanism. Activation of the $A_{2B}$ AR is involved in this process. Selective $A_{2B}$ antagonists are expected to have beneficial effect on pulmonary fibrosis (Curr. Drug Targets, 2006, 7, 699-706; Am. J. Resper. Cell. Mol. Biol., 2005, 32, 228). $A_{2B}$ antagonists can be used as wound healing agents. Activation of the $A_{2B}$ AR promotes angiogenesis by increasing the release of angiogenic factors and $A_{2B}$ antagonists are useful to block angiogenesis (Circ. Res., 2002, 90, 531-538). $A_{2B}$ AR may be involved in the inhibition cardiac fibroblast (CF) proliferation (Am. J. Physiol. Heart Circ. Physiol., 2004, 287, H2478-H2486). Adenosine stimulates Cl-secretion in the intestinal epithelia pointing towards a possible treatment for cystic fibrosis patients with CFTR mutation (Am. J. Respir. Cell Mol. Biol., 2008, 39, 190-197). High affinity $A_{2B}$ antagonists are effective in hot plate model suggestive of the role of $A_{2B}$ in nociception and can be used as potential analgesic agents (The J. of Pharmacol. and Exp. Ther., 2004, 308, 358-366).

$A_{2B}$ receptor is involved in release of IL-6. Increasing evidence suggests that IL-6 plays a role in Alzheimer's disease in the context of inflammatory process associated with disease. Hence $A_{2B}$ receptor antagonist might be useful for Alzheimer's disease. The $A_{2B}$ ARs are involved in the stimulation of nitric oxide production during Na$^+$-linked glucose or glutamine absorption. They are involved in glucose production in hepatocytes upon agonist stimulation. $A_{2B}$-receptor antagonists showed an anti-diabetic potential mainly by increasing plasma insulin levels under conditions when the adenosine tonus was elevated in-vivo and increased insulin release in-vitro (J. Pharm. Pharmacol. 2006 December; 58(12):1639-45). Thus $A_{2B}$ antagonists may serve as a novel target for the treatment of this metabolic disease.

It has been demonstrated that adenosine activation of the $A_{2B}$ adenosine receptor increase cAMP accumulation, cell proliferation and VEGF expression in human retinal endothelial cells. Activation of $A_{2B}$AdoR increased vascular endothelial cell growth factor mRNA and protein expression in human retinal endothelial cells. Adenosine also has a synergistic effect with VEGF on retinal endothelial cell proliferation and capillary morphogenesis in vitro. Such activity is necessary in healing wounds, but the hyperproliferation of endothelial cells promotes diabetic retinopathy. Also, an undesirable increase in blood vessels occurs in neoplasia. Accordingly, inhibition of binding of adenosine to $A_{2B}$ receptors in the endothelium will alleviate or prevent hypervasculation, thus preventing retinopathy and inhibiting tumor formation.

In view of the physiological effects mediated by adenosine receptor, several A2B receptor antagonists have been recently disclosed for the treatment or prevention of asthma, bronchoconstriction, allergic diseases, hypertension, atherosclerosis, reperfusion injury, myocardial ischemia, retinopathy, inflammation, gastrointestinal tract disorders, cell proliferation diseases and/or diabetes mellitus. See for example WO2008002902, WO2007149277, WO2007017096, WO2007109547, WO2006091896, WO2006015357, WO2005042534, WO2005021548, WO2004106337, WO2003000694, WO2003082873, WO2003006465, WO2003053361, WO2003002566, WO2003063800, WO2003042214, WO2003035639, EP1283056, WO0200073307, WO0200125210, WO2000073307, US20050119287, US20060281927.

Recent findings in Nature Medicine, 2011 suggests elevated levels of adenosine and 2,3-DPG in the blood of Sickle Cell Disease (SCD) transgenic mice at steady state. These findings led to the discovery that elevated adenosine signaling through $A_{2B}R$ promotes sickling by inducing 2,3-DPG production. Lowering adenosine concentrations or interfering with activation of $A_{2B}R$ reduced sickling, hemolysis and tissue injury in SCD transgenic mice both at steady state and during an acute crisis event. Both adenosine and 2,3-DPG concentrations were elevated in the blood of individuals with SCD, and it was shown that adenosine signaling through the A2BR increases 2,3-DPG concentrations and induces sickling of RBCs derived from humans with SCD. These findings provide evidence for the pathogenic consequences of excessive adenosine signaling in SCD and suggest that interfering with adenosine signaling (particularly with $A_{2B}R$ activation on erythrocytes) may be an effective mechanism-based therapy for preventing sickling and hemolysis in individuals with SCD and ultimately for reducing the life-threatening complications associated with SCD. Thus $A_{2B}$ antagonists may serve as a novel target for the treatment of SCD.

Indian patent application No. 571/CHE/2009 discloses $A_{2B}$ adenosine receptor antagonists that are potent and selective for the $A_{2B}$ adenosine receptor. Such compounds are known to be relatively insoluble in aqueous media and difficult to formulate at higher doses using conventional pharmaceutical excipients. It has been surprisingly found that the compounds of the present disclosure which are more soluble in aqueous media and/or conventional pharmaceutical excipients are active prodrugs of the compounds disclosed in 571/CHE/2009. The compounds of the present disclosure, thereby make it possible to formulate at higher doses in a manner that provides sufficient plasma levels of the compound for development.

SUMMARY

The present disclosure provides compounds of formula I and II, or its tautomers, polymorphs, stereoisomers, solvates or a pharmaceutically acceptable salts thereof, pharmaceutical compositions containing them and methods of treating conditions and diseases that are mediated by adenosine $A_{2B}$ receptor activity,

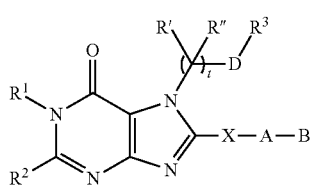

Formula I

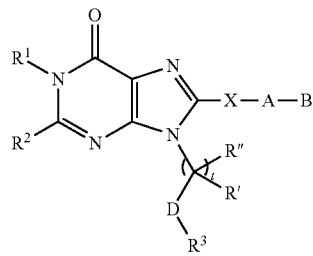

Formula II wherein
$R^1$ is an alkyl wherein one or more methylene groups are optionally replaced by hetero atoms or a group selected from —O—, —S(O)$_p$—, —N(R$^a$)—, or —C(O), provided that the heteroatom is not adjacent to N in the ring; p is selected from 0, 1 or 2;
wherein alkyl is unsubstituted or substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, -aminocarbonylamino, hydroxyamino, alkoxyamino;
$R^2$ is selected from the group consisting of hydrogen, halogen, cyano, nitro, carboxy, acyl, aminocarbonyl, alkyl, alkenyl, alkynyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl and heteroaryloxy;
wherein alkyl, alkenyl, alkynyl, alkoxy, carboxyalkyl, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl, heteroaryloxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;
wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^d$;
R' and R" are independently selected from hydrogen, or alkyl; or
R' and R" taken together may represent O, or a lower cycloalkyl ring system which is saturated or partially unsaturated;
$R^3$ is selected from the group consisting of alkyl, aryl, —C(O)R$^4$ and —P(O)(OR$^5$)$_2$;
$R^4$ is selected from alkyl, alkoxy, aryl, heteroaryl, heterocyclyl, or —NR$^6$R$^7$;
$R^5$ is selected from hydrogen, alkyl, aryl, arylalkyl, —CH$_2$OC(O)alkyl, or —CH$_2$OC(O)Oalkyl; or two R$^5$ groups taken together form a five or six membered ring system which is saturated or partially unsaturated and is optionally substituted with 1 to 4 substituents independently selected from halo, alkyl, aryl or heteroaryl;

$R^6$ and $R^7$ are independently selected from the group consisting of hydrogen, alkyl, heterocyclyl and heterocyclylalkyl; or $R^6$ and $R^7$ taken together form a monocyclic ring system which is saturated or partially unsaturated and optionally have additional heteroatoms selected from O, N or S, wherein the ring system is optionally substituted with 1 to 4 substituents independently selected from halo, alkyl, alkoxy, or —$NR^8R^9$;

$R^4$, $R^5$, $R^6$ and $R^7$ is optionally substituted with 1 to 4 substituents independently selected from hydroxyl, halogen, alkyl, alkoxy, haloalkyl, —$NR^8R^9$, —C(O)$OR^{10}$, —OC(O)$R^{10}$ or —NC(O)$R^{10}$;

$R^8$ and $R^9$ are independently selected from the group consisting of hydrogen and alkyl;

$R^{10}$ is selected from hydrogen, hydroxy, halogen, amino, substituted amino, cyano, alkyl, alkoxy, haloalkyl, haloalkoxy, carboxy, carboxyalkyl, aminocarbonyl, aryl or arylalkyl;

X is an optionally substituted arylene or an optionally substituted heteroarylene;

A is selected from a bond, or ($C_1$-$C_6$)alkylene, wherein 1 to 4 methylene groups are optionally replaced by group independently selected from O, —S(O)$_p$—, —N($R^b$)—, or —C(O)—;

wherein alkylene is unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$$NR^cR^c$, —$NR^cS(O)_2R^c$ or —S(O)$_pR^d$;

wherein each substituent is unsubstituted or substituted with 1, 2, or 3 substituents independently selected from alkyl, carboxy, carboxyalkyl, aminocarbonyl, hydroxy, alkoxy, halogen, CF, amino, substituted amino, cyano or —S(O)$_pR^d$;

B is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —S(O)$_2$$NR^bR^b$, —$NR^bS(O)_2R^b$ or —S(O)$_pR^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_pR^d$;

D is selected from —O—, —S(O)$_p$— or —N($R^a$)—;

$R^a$ is hydrogen or an alkyl;

$R^b$ is selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

$R^c$ is selected from hydrogen, alkyl, aryl, heteroaryl or heterocyclyl;

$R^d$ is selected from alkyl, cycloalkyl, aryl, heterocyclyl or heteroaryl;

p is 0, 1 or 2; and t is 1 or 2.

The present disclosure also relates to a method of using the compounds of Formula I and II for treating a disease state in a mammal that is alleviable by treatment with an $A_{2B}$ adenosine receptor antagonist.

The present disclosure further relates to methods for preparing the compounds of Formula I and II.

The present disclosure also relates to pharmaceutical formulations, comprising a therapeutically effective amount of a compound of Formula I and II and at least one pharmaceutically acceptable excipient.

These and other features, aspects, and advantages of the present subject matter will become better understood with reference to the following description. This summary is provided to introduce a selection of concepts in a simplified form. This summary is not intended to identify key features or essential features of the subject matter, nor is it intended to be used to limit the scope of the subject matter.

DETAILED DESCRIPTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —CH($CH_3$)$CH_2$—) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2;

or 2) an alkyl group or alkylene group as defined above that is interrupted by 1, 2, 3, 4, 5, 6, 7, 8, 9 or 10 atoms independently selected from oxygen, sulfur and NR$^d$, where R$^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, CF$_3$, amino, substituted amino, cyano, or —S(O)$_p$R$^c$, in which R$^c$ is alkyl, aryl, or heteroaryl and p is 0, 1, or 2;

or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo [2.2.1] heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH$_2$C≡CH), homopropargyl (or but-1-yn-4-yl, —CH$_2$CH$_2$C≡CH) and the like.

The term "alkynylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —SO$_3$H, aryl, aryloxy, hetzroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$ where R$^c$ is alkyl, aryl, or heteroaryl and p is 0, 1 or 2.

The term "cycloalkyl" refers to carbocyclic groups of from 3 to 20 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo [2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)$_p$R$^b$, where R is hydrogen, hydroxyl, alkoxy, alkyl and cycloalkyl, heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'''—O—, where R''' is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —S(O)$_p$R$^c$, where R$^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to ($C_{1-6}$)alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$ NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —S(O)$_p$R$^c$ where R$^c$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R" where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)OR$^d$ where R$^d$ is alkyl, cycloalkyl, where alkyl, cycloalkyl are as defined herein, and may be optionally further substituted by alkyl, halogen, $CF_3$, amino, substituted amino, cyano, or —$S(O)_pR^c$, in which $R^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4] oxadiazole, [1,3,4] oxadiazole, [1,2,4] thiadiazole, [1,3,4] thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, pherianthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where $R^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_nR^c$, where $R^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl, pyrrolidinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cycloalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —$S(O)_pR^b$, where $R^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)R^c$, where $R^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —$S(O)_2R$.

The term "substituted sulfone" refers to a group —$S(O)_2R$, in which R is alkyl, aryl, or heteroaryl.

The compounds of the present disclosure may have the ability to crystallize in more than one form, a characteristic known as polymorphism, and all such polymorphic forms ("polymorphs") are encompassed within the scope of the present disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the present disclosure are congeners, analogs, hydrolysis products, metabolites and precursor of the compound. In general, unless otherwise indicated, all physical forms are equivalent for the uses contemplated herein and are intended to be within the scope of the present invention "Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the present disclosure are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present disclosure are inert organic solvents. The term "q.s." means adding a quantity sufficient to achieve a stated function, e.g., to bring a solution to the desired volume (i.e., 100%).

The present disclosure provides compounds of formula I or formula II, or its tautomers, polymorphs, stereoisomers, solvates or a pharmaceutically acceptable salts thereof, pharmaceutical compositions containing them and methods of treating conditions and diseases that are mediated by adenosine $A_{2B}$ receptor activity,

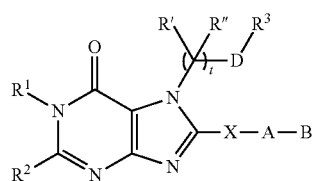

Formula I

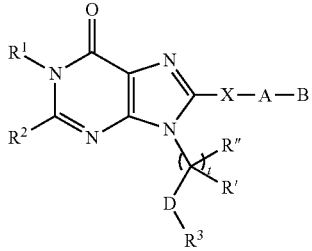

Formula II wherein $R^1$ is an alkyl, wherein one or more methylene groups are optionally replaced by hetero atoms or a group selected from —O—, —S(O)$_p$—, —N($R^a$)—, or —C(O), provided that the heteroatom is not adjacent to N in the ring; p is selected from 0, 1 or 2;
  wherein alkyl is unsubstituted or substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, -aminocarbonylamino, hydroxyamino or alkoxyamino;

$R^2$ is selected from the group consisting of hydrogen, halogen, cyano, nitro, carboxy, acyl, aminocarbonyl, alkyl, alkenyl, alkynyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl and heteroaryloxy;
  wherein alkyl, alkenyl, alkynyl, alkoxy, carboxyalkyl, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl, heteroaryloxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;
  wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^d$;

R' and R" are independently selected from hydrogen, or alkyl; or

R' and R" taken together may represent O, or a lower cycloalkyl ring system which is saturated or partially unsaturated;

$R^3$ is selected from the group consisting of alkyl, aryl, —C(O)R$^4$ and —P(O)(OR$^5$)$_2$;

$R^4$ is selected from the group consisting of alkyl, alkoxy, aryl, heteroaryl, heterocyclyl and —NR$^6$R$^7$;

$R^5$ is selected from hydrogen, alkyl, aryl, arylalkyl, —CH$_2$OC(O)alkyl, or —CH$_2$OC(O)Oalkyl, or two R$^5$ groups taken together form a five or six membered ring system which is saturated or partially unsaturated and is optionally substituted with 1 to 4 substituents independently selected from halo, alkyl, aryl or heteroaryl;

$R^6$ and $R^7$ are independently selected from the group consisting of hydrogen, alkyl, heterocyclyl and heterocyclylalkyl, or $R^6$ and $R^7$ taken together form a monocyclic ring system which is saturated or partially unsaturated and optionally have additional heteroatoms selected from O, N or S, wherein the ring system is optionally substituted with 1 to 4 substituents independently selected from halo, alkyl, alkoxy or —NR$^8$R$^9$;

$R^4$, $R^5$, $R^6$ and $R^7$ is optionally substituted with 1 to 4 substituents independently selected from hydroxyl, halogen, alkyl, alkoxy, haloalkyl, —NR$^8$R$^9$, —C(O)OR$^{10}$, —OC(O)R$^{10}$ or —NC(O)R$^{10}$;

R$^8$ and R$^9$ are independently selected from the group consisting of hydrogen and alkyl;

R$^{10}$ is selected from a group consisting of hydrogen, hydroxy, halogen, amino, substituted amino, cyano, alkyl, alkoxy, haloalkyl, haloalkoxy, carboxy, carboxyalkyl, aminocarbonyl, aryl and arylalkyl;

X is an optionally substituted arylene or an optionally substituted heteroarylene;

A is selected from a bond, or (C$_1$-C$_6$)alkylene, wherein 1 to 4 methylene groups are optionally replaced by group independently selected from O, —S(O)$_p$—, —N(R$^b$)—, or —C(O)—;
   wherein alkylene is unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;
      wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

B is selected from hydrogen, heterocyclyl, cycloalkyl, aryl or heteroaryl;
   wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —S(O)$_2$NR$^b$R$^b$, —NR$^b$S(O)$_2$R$^b$ or —S(O)$_p$R$^d$;
      wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

D is selected from —O—, —S(O)$_p$— or —N(R$^a$)—;
   R$^a$ is hydrogen or an alkyl;
   R$^b$ is selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;
   R$^c$ is selected from hydrogen, alkyl, aryl, heteroaryl or heterocyclyl;
   R$^d$ is selected from alkyl, cycloalkyl, aryl, heterocyclyl or heteroaryl;
   p is 0, 1 or 2; and
   t is 1 or 2.

The compounds of the present disclosure are surprisingly found to be more soluble in aqueous media and/or conventional pharmaceutical excipients are active prodrugs of the A$_{2B}$ adenosine receptor antagonists compounds. Hence these present compounds facilitates in providing higher plasma level of the active moiety. The compounds of the present disclosure, thereby make it possible to formulate at higher doses in a manner that provides sufficient plasma levels of the compound for development.

According to another embodiment, the present disclosure relates to compounds of formula (I) or formula (II) or its tautomers, polymorphs, stereoisomers, solvates or a pharmaceutically acceptable salts thereof, wherein, R$^1$ is an alkyl, wherein alkyl is unsubstituted or substituted with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, -aminocarbonylamino, hydroxyamino or alkoxyamino;

R$^2$ is selected from the group consisting of hydrogen, halogen, cyano, nitro, alkyl, hydroxyalkyl, haloalkyl, haloalkyloxy, alkoxy, —NR$^b$R$^b$ and —S(O)$_p$R$^b$;
   wherein alkyl and R$^b$ are unsubstituted or substituted independently with alkyl, alkoxy, acyl, acylamino, acyloxy, nitro, amino, monoalkylamino, dialkylamino, hydroxyamino, alkoxyamino, aminocarbon) iamino, azido, cyano, halogen, hydroxy, hydroxyalkyl, keto, thiocarbonyl, carboxy, alkylcarboxy, carboxyalkyl, —SO$_3$H, aminocarbonyl, alkoxycarbonylamino, —S(O)$_2$NR$^c$R$^c$, —NR$^c$S(O)$_2$R$^c$ or —S(O)$_p$R$^d$;

R' and R" are independently selected from hydrogen, or alkyl; or

R' and R" taken together may represent 0, or a lower cycloalkyl ring system which is saturated or partially unsaturated;

R$^3$ is selected from the group consisting of alkyl, aryl, —C(O)R$^4$ and —P(O)(OR$^5$)$_2$;

R$^4$ is selected from the group consisting of alkyl, alkoxy, aryl, heteroaryl, heterocyclyl and —NR$^6$R$^7$;

R$^5$ is selected from the group consisting of hydrogen, alkyl, aryl, arylalkyl, —CH$_2$OC(O)alkyl, and —CH$_2$OC(O)Oalkyl, or two R$^5$ groups taken together may form a five or six membered ring system which is saturated or partially unsaturated and may further be optionally substituted with 1 to 4 substituents independently selected from halo, alkyl, aryl or heteroaryl;

R$^6$ and R$^7$ are independently selected from the group consisting of hydrogen, alkyl, heterocyclyl and heterocyclylalkyl; or R$^6$ and R$^7$ taken together form a monocyclic ring system which is saturated or partially unsaturated and optionally have additional heteroatoms selected from O, N or S, wherein the ring system is optionally substituted with 1 to 4 substituents independently selected from halo, alkyl, alkoxy or —NR$^8$R$^9$;

R$^4$, R$^5$, R$^6$ and R$^7$ is optionally substituted with 1 to 4 substituents independently selected from hydroxyl, halogen, alkyl, alkoxy, haloalkyl, —NR$^8$R$^9$, —C(O)OR$^{10}$, —OC(O)R$^{10}$ or —NC(O)R$^{10}$;

R$^8$ and R$^9$ are independently selected from the group consisting of hydrogen and alkyl;

R$^{10}$ is selected from the group consisting of hydrogen, hydroxy, halogen, amino, substituted amino, cyano, alkyl, alkoxy, haloalkyl, haloalkoxy, carboxy, carboxyalkyl, aminocarbonyl, aryl and arylalkyl;

X is an optionally substituted arylene or an optionally substituted heteroarylene;

A is selected from a bond, or (C$_1$-C$_6$)alkylene, wherein 1 to 4 methylene groups are optionally replaced by groups independently selected from O, —S(O)$_p$—, —N(R$^b$)—, or —C(O)—;

B is selected from hydrogen, heterocyclyl, cycloalkyl, aryl or heteroaryl;

wherein heterocyclyl, cycloalkyl, aryl and heteroaryl are unsubstituted or substituted independently with alkyl, alkoxy, cycloalkyl, cycloalkylalkyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

D is selected from —O—, —S(O)$_p$— or —N(R$^a$)—,

R$^a$ is hydrogen or an alkyl;

R$^b$ is selected from the group consisting of hydrogen, alkyl, acyl, carboxyalkyl and carbonylamino; R$^c$ is selected from hydrogen, alkyl, aryl, heteroaryl or heterocyclyl;

R$^d$ is selected from alkyl, cycloalkyl, aryl, heterocyclyl or heteroaryl;

p is 0, 1 or 2; and t is 1 or 2.

According to another embodiment, the present disclosure relates to compounds of formula (I) or formula (II) or its tautomers, polymorphs, stereoisomers, solvates or a pharmaceutically acceptable salts thereof, wherein, R$^1$ is an alkyl;

R$^2$ is selected from the group cons ting of hydrogen, halogen, cyano, nitro, alkyl, hydroxyalkyl, haloalkyl, haloalkyloxy alkoxy;

R' and R" are independently selected from hydrogen, or alkyl; or

R' and R" taken together may represent O, or a lower cycloalkyl ring system which is saturated or partially unsaturated;

R$^3$ is selected from the group consisting of alkyl, aryl, —C(O)R$^4$ and —P(O)(OR$^5$)$_2$;

R$^4$ is selected from the group consisting of alkyl, alkoxy, aryl, heteroaryl, heterocyclyl and —NR$^6$R$^7$;

R$^5$ is selected from the group consisting of hydrogen, alkyl, aryl, arylalkyl, —CH$_2$OC(O)alkyl, and —CH$_2$OC(O)Oalkyl or two R$^5$ groups taken together may form a five or six membered ring system which is saturated or partially unsaturated and is optionally substituted with 1 to 4 substituents independently selected from halo, alkyl, aryl or heteroaryl;

R$^6$ and R$^7$ are independently selected from the group consisting of hydrogen, alkyl, heterocyclyl and heterocyclylalkyl, or R$^6$ and R$^7$ taken together form a monocyclic ring system which is saturated or partially unsaturated and optionally have additional heteroatoms selected from O, N or S, wherein the ring system is optionally substituted with 1 to 4 substituents independently selected from halo, alkyl, alkoxy or —NR$^8$R$^9$;

R$^4$, R$^5$, R$^6$ and R$^7$ is optionally substituted with 1 to 4 substituents independently selected from hydroxyl, halogen, alkyl, alkoxy, haloalkyl, —NR$^8$R$^9$, —C(O)OR$^{10}$, —OC(O)R$^{10}$ or —NC(O)R$^{10}$;

R$^8$ and R$^9$ are independently selected from the group consisting of hydrogen and alkyl;

R$^{10}$ is selected from the group consisting of hydrogen, hydroxy, halogen, amino, substituted amino, cyano, alkyl, alkoxy, haloalkyl, haloalkoxy, carboxy, carboxyalkyl, aminocarbonyl, aryl and arylalkyl;

X is an optionally substituted arylene or an optionally substituted heteroarylene;

A is selected from a bond or (C$_1$-C$_6$)alkylene;

B is selected from aryl or heteroaryl;

wherein aryl and heteroaryl are unsubstituted or substituted independently with alkyl, alkoxy, acyl, acylamino, acyloxy, amino, monoalkylamino, dialkylamino, aminocarbonyl, alkoxycarbonylamino, azido, cyano, halogen, hydroxy, hydroxyalkyl, haloalkyl, perhaloalkyl, keto, thiocarbonyl, carboxy, alkylcarboxy, carboxyalkyl, carboxyalkyloxy, alkylcarboxyalkyloxy —SO$_3$H, aminocarbonylamino, hydroxyamino, alkoxyamino, nitro, —S(O)$_2$NR$^b$R$^b$, —NR$^b$S(O)$_2$R$^b$ or —S(O)$_p$R$^d$;

D is selected from —O—, —S(O)$_p$— or —N(R$^a$)—;

R$^a$ is hydrogen or an alkyl;

R$^b$ is selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

R$^c$ is selected from hydrogen, alkyl, aryl, heteroaryl or heterocyclyl;

R$^d$ is selected from alkyl, cycloalkyl, aryl, heterocyclyl or heteroaryl;

p is 0, 1 or 2; and t is 1 or 2.

According to another embodiment, the present disclosure relates to compounds of formula (I) or formula (II) or its tautomers, polymorphs, stereoisomers, solvates or a pharmaceutically acceptable salts thereof, wherein, R$^1$ is an alkyl;

R$^2$ is selected from the group consisting of hydrogen, halogen, cyano, nitro, alkyl, hydroxyalkyl, haloalkyl, haloalkyloxy and alkoxy;

R' and R" are independently selected from hydrogen or alkyl;

R$^3$ is selected from the group consisting of alkyl, —C(O)R$^4$ and —P(O)(OR$^5$)$_2$;

R$^4$ is selected from alkyl or alkoxy;

R$^5$ is selected from the group consisting of hydrogen, alkyl, —CH$_2$OC(O)alkyl or —CH$_2$OC(O)Oalkyl;

R$^4$ and R$^5$ is optionally substituted with 1 to 4 substituents independently selected from hydroxyl, halogen, alkyl, alkoxy, haloalkyl, —NR$^8$R$^9$, —C(O)OR$^{10}$, —OC(O)R$^{10}$ or —NC(O)R$^{10}$;

R$^8$ and R$^9$ are independently selected from the group consisting of hydrogen and alkyl;

R$^{10}$ is selected from the group consisting of hydrogen, hydroxy, halogen, amino, substituted amino, cyano, alkyl, alkoxy, haloalkyl, haloalkoxy, carboxy, carboxyalkyl, aminocarbonyl, aryl and arylalkyl;

X is optionally substituted heteroarylene;

A is selected from a bond or (C$_1$-C$_6$)alkylene;

B is selected from aryl or heteroaryl;

wherein aryl and heteroaryl are unsubstituted or substituted independently with alkyl, alkoxy, acyl, acylamino, acyloxy, amino, monoalkylamino, dialkylamino, aminocarbonyl, alkoxycarbonylamino, azido, cyano, halogen, hydroxy, hydroxyalkyl, haloalkyl, perhaloalkyl, keto, thiocarbonyl, carboxy, alkylcarboxy, carboxyalkyl, carboxyalkyloxy, alkylcarboxyalkyloxy —$SO_3H$, aminocarbonylamino, hydroxyamino, alkoxyamino or nitro;

D is selected from —O—, —$S(O)_p$— or —$N(R^a)$—;

$R^a$ is hydrogen or an alkyl;

p is 0, 1 or 2; and t is 1 or 2.

According to an embodiment of the present disclosure, X is heteroarylene.

According to another embodiment of the present disclosure, B is substituted aryl;

In another embodiment of the present disclosure, $R^1$ is alkyl.

According to another embodiment of the present disclosure, $R^2$ is selected from a group consisting of hydrogen, halogen, cyano, unsubstituted or substituted cycloalkyl and unsubstituted or substituted heteroaryl.

Particular embodiments of the present disclosure are compounds or its tautomers, polymorphs, stereoisomers, solvate or a pharmaceutically acceptable salts thereof, selected from the group consisting of, Phosphoric acid mono-{2-cyano-6-oxo-1-propyl-8-[1-(3-trifluoromethyl-benzyl)-1H-pyrazol-4-yl]-3,6-dihydro-purin-7-ylmethyl}ester, Phosphoric acid mono-{2-cyano-6-oxo-1-propyl-8-[1-(3-trifluoromethyl-benzyl)-1H-pyrazol-4-yl]-1,6-dihydro-purin-9-ylmethyl}ester di sodium salt, Phosphoric acid mono-{2-chloro-6-oxo-1-propyl-8-[1-(3-trifluoromethyl-benzyl)-1H-pyrazol-4-yl]-1,6-dihydro-purin-7-ylmethyl}ester, Phosphoric acid mono-{2-chloro-6-oxo-1-propyl-8-[1-(3-trifluoromethyl-benzyl)-1H-pyrazol-4-yl]-1,6-dihydro-purin-9-ylmethyl}ester, 2,2-Dimethyl-propionic acid 6-oxo-1-propyl-8-[1-(3-trifluoromethyl-benzyl)-1H-pyrazol-4-yl]-1,6-dihydro-purin-7-ylmethyl ester, 2,2-Dimethyl-propionic acid 6-oxo-1-propyl-8-[1-(3-trifluoromethyl-benzyl)-1H-pyrazol-4-yl]-1,6-dihydro-purin-9-ylmethyl ester.

2,2-Dimethyl-propionic acid 2-chloro-6-oxo-1-propyl-8-[1-(3-trifluoromethyl-benzyl)-1H-pyrazol-4-yl]-1,6-dihydro-purin-7-ylmethyl ester, 7-Methoxymethyl-1-propyl-8-[1-(3-trifluoromethyl-benzyl)-1H-pyrazol-4-yl]-1,7-dihydro-purin-6-one, 9-Methoxymethyl-1-propyl-8-[1-(3-trifluoromethyl-benzyl)-1H-pyrazol-4-yl]-1,9-dihydro-purin-6-one, 2-Chloro-7-methoxymethyl-1-propyl-8-[1-(3-trifluoromethyl-benzyl)-1H-pyrazol-4-yl]-1,7-dihydro-purin-6-one, Phosphoric acid mono-{6-oxo-1-propyl-8-[1-(3-trifluoromethyl-benzyl)-1H-pyrazol-4-yl]-1,6-dihydro-purin-7-ylmethyl}ester, (2-Dimethylamino-ethyl)-methyl-carbamic acid 6-oxo-1-propyl-8-[1-(3-trifluoromethyl-benzyl)-1H-pyrazol-4-yl]-1,6-dihydro-pyrin-7-ylmethyl ester, (1-Ethyl-pyrrolidin-2-ylmethyl)-carbamic acid 6-oxo-1-propyl-8-[1-(3-trifluoromethyl-benzyl)-1H-pyrazol-4-yl]-1,6-dihydro-purin-7-ylmethyl ester, Nicotinic acid 6-oxo-1-propyl-8-[1-(3-trifluoromethyl-benzyl)-1H-pyrazol-4-yl]-1,6-dihydro-purin-7-ylmethyl ester, Acetic acid 6-oxo-1-propyl-8-[1-(3-trifluoromethyl-benzyl)-1H-pyrazol-4-yl]-1,6-dihydro-purin-7-ylmethyl ester, Butyric acid 6-oxo-1-propyl-8-[1-(3-trifluoromethyl-benzyl)-1H-pyrazol-4-yl]-1,6-dihydro-purin-7-ylmethyl ester, Butyric acid 2-chloro-6-oxo-1-propyl-8-[1-(3-trifluoromethyl-benzyl)-1H-pyrazol-4-yl]-1,6-dihydro-purin-7-ylmethyl ester, Nicotinic acid 2-chloro-6-oxo-1-propyl-8-[1-(3-trifluoromethyl-benzyl)-1H-pyrazol-4-yl]-1,6-dihydro-purin-7-ylmethyl ester, (2-Dimethylamino-ethyl)-methyl-carbamic acid 2-chloro-6-oxo-1-propyl-8-[1-(3-trifluoromethyl-benzyl)-1H-pyrazol-4-yl]-1,6-dihydro-purin-7-ylmethyl ester, (2-Dimethylamino-ethyl)-methyl-carbamic acid 2-cyano-6-oxo-1-propyl-8-[1-(3-trifluoromethyl-benzyl)-1H-pyrazol-4-yl]-1,6-dihydro-purin-7-ylmethyl ester, Butyric acid 2-cyano-6-oxo-1-propyl-8-[1-(3-trifluoromethyl-benzyl)-1H-pyrazol-4-yl]-1,6-dihydro-purin-7-ylmethyl ester, 2,2-Dimethyl-propionic acid 2-cyano-6-oxo-1-propyl-8-[1-(3-trifluoromethyl-benzyl)-1H-pyrazol-4-yl]-1,6-dihydro-purin-7-ylmethyl ester, Nicotinic acid 2-cyano-6-oxo-1-propyl-8-[1-(3-trifluoromethyl-benzyl)-1H-pyrazol-4-yl]-1,6-dihydro-purin-7-ylmethyl ester, 4-Methyl-piperazine-1-carboxylic acid 2-cyano-6-oxo-1-propyl-8-[1-(3-trifluoromethyl-benzyl)-1H-pyrazol-4-yl]-1,6-dihydro-purin-7-ylmethyl ester, 1-{6-oxo-7-phosphonooxymethyl-1-propyl-8-[1-(3-trifluoromethyl-benzyl)-1H-pyrazol-4-yl]-6,7-dihydro-1H-purin-2-yl}-pyrrolidine-2-carboxylic acid, 1-{7-(2,2-Dimethyl-propionyloxymethyl)-6-oxo-1-propyl-8-[1-(3-trifluoromethyl-benzyl)-1H-pyrazol-4-yl]-6,7-dihydro-1H-purin-2-yl}-pyrrolidine-2-carboxylic acid, 2,2-Dimethyl-propionic acid 2-cyclopropyl-6-oxo-1-propyl-8-[1-(3-trifluoromethyl-benzyl)-1H-pyrazol-4-yl]-1,6-dihydro-purin-7-ylmethyl ester, Phosphoric acid mono-{2-cyclopropyl-6-oxo-1-propyl-8-[1-(3-trifluoromethyl-benzyl)-1H-pyrazol-4-yl]-1,6-dihydro-purin-7-ylmethyl}ester, Phosphoric acid mono-{2-chloro-6-oxo-1-propyl-8-[1-(6-trifluoromethyl-pyridin-3-ylmethyl)-1H-pyrazol-4-yl]-1,6-dihydro-purin-7-ylmethyl}ester, Phosphoric acid mono-{6-oxo-1-propyl-8-[1-(6-trifluoromethyl-pyridin-3-ylmethyl)-1H-pyrazol-4-yl]-1,6-dihydro-purin-7-ylmethyl}ester, Benzoic acid 2-cyano-6-oxo-1-propyl-8-[1-(3-trifluoromethyl-benzyl)-1H-pyrazol-4-yl]-1,6-dihydro-purin-7-ylmethyl ester, 7-Methoxymethyl-6-oxo-1-propyl-8-[1-(3-trifluoromethyl-benzyl)-1H-pyrazol-4-yl]-6,7-dihydro-1H-purine-2-carbonitrile, Acetic acid 2-cyano-6-oxo-1-propyl-8-[1-(3-trifluoromethyl-benzyl)-1H-pyrazol-4-yl]-1,6-dihydro-purin-7-ylmethyl ester, (S)-Pyrrolidine-1,2-dicarboxylic acid 1-benzyl ester 2-{2-cyano-6-oxo-1-propyl-8-[1-(3-trifluoromethyl-benzyl)-1H-pyrazol-4-yl]-1,6-dihydro-purin-7-ylmethyl}ester, Butyric acid 2-cyano-6-oxo-1-propyl-8-[1-(3-trifluoromethyl-benzyl)-1H-pyrazol-4-yl]-1,6-dihydro-purin-9-ylmethyl ester, Butyric acid 2-cyclopropyl-6-oxo-1-propyl-8-[1-(3-trifluoromethyl-benzyl)-1H-pyrazol-4-yl]-1,6-dihydro-purin-9-ylmethyl ester, Butyric acid 2-chloro-6-oxo-1-propyl-8-[1-(3-trifluoromethyl-benzyl)-1H-pyrazol-4-yl]-1,6-dihydro-purin-9-ylmethyl ester, Butyric acid 6-oxo-1-propyl-8-[1-(3-trifluoromethyl-benzyl)-1H-pyrazol-4-yl]-1,6-dihydro-purin-9-ylmethyl ester, Phosphoric acid mono-{2-fluoro-6-oxo-1-propyl-8-[1-(3-trifluoromethyl-benzyl)-1H-pyrazol-4-yl]-1,6-dihydro-purin-9-ylmethyl}ester, Phosphoric acid mono-{6-oxo-1-propyl-8-[1-(3-trifluoromethyl-benzyl)-1H-pyrazol-4-yl]-1,6-dihydro-purin-9-ylmethyl}ester, or Phosphoric acid mono-{2-cyclopropyl-6-oxo-1-propyl-8-[1-(3-trifluoromethyl-benzyl)-1H-pyrazol-4-yl]-1,6-dihydro-purin-9-ylmethyl}ester.

Another embodiment of the present disclosure relates to a compound of formula (I) or formula (II) or its tautomers, polymorphs, stereoisomers, solvates or a pharmaceutically acceptable salts thereof, for treating disease or disorder susceptible to improvement by antagonism of $A_{2B}$ receptor. Yet another embodiment of the present disclosure relates to a compound of formula (I) or formula (II) or its tautomers, polymorphs, stereoisomers or a pharmaceutically acceptable salts thereof, for treating asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders including inflammatory bowel disease, sickel cell disease, and/or autoimmune diseases.

Still another embodiment of the present disclosure also relates to a compound of formula (I) or formula (II) or its tautomers, polymorphs, stereoisomers, solvates or a pharmaceutically acceptable salts thereof, for use in treatment of conditions mediated by adenosine receptor.

The present disclosure also relates to a method of treating a disease in a mammal that is alleviable by treatment with an $A_{2B}$ adenosine receptor antagonist comprising administering a therapeutically effective amount of the compounds of Formula I or II, or its tautomers, polymorphs, stereoisomers, solvates or a pharmaceutically acceptable salts thereof.

The present disclosure also relates to a method of treating a disease state in a mammal that is alleviable by treatment with an $A_{2B}$ adenosine receptor antagonist comprising administering a therapeutically effective amount of the compounds of Formula I or II, or its tautomers, polymorphs, stereoisomers, solvates or a pharmaceutically acceptable salts thereof, in particular treatment, prevention or suppression of diseases and disorders that may be susceptible to improvement by antagonism of the adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders including inflammatory bowel disease, neurodegenerative disorders and/or autoimmune diseases.

The present disclosure further relates to the process of preparation of compounds of formula I and formula II, or pharmaceutically acceptable salts thereof.

Another embodiment of the present disclosure relates to a process for the preparation of a compound of formula (I) or formula (II), or its tautomers, polymorphs, stereoisomers, solvates or a pharmaceutically acceptable salts thereof, said process comprising: reacting diamine of formula (1a)

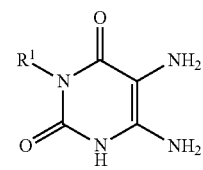

with an acid of formula (1b) or its acid chloride

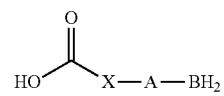

to obtain a compound of formula (1c);

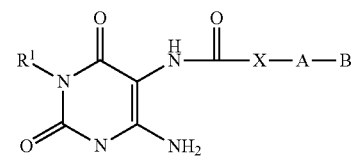

cyclising compound of formula (1c) to obtain compound of formula (1d);

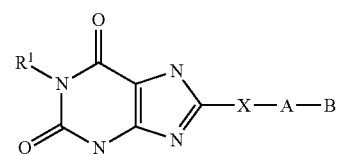

converting compound of formula (1d) to a compound of formula (1e);

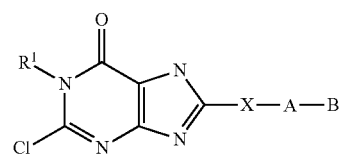

converting compound of formula (1e) to compound of formula (1f);

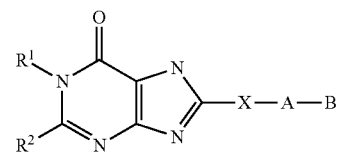

compound of formula (1f) is reacted with compound of formula (1g)

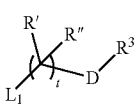

to obtain compound of formula (I) and formula (II)

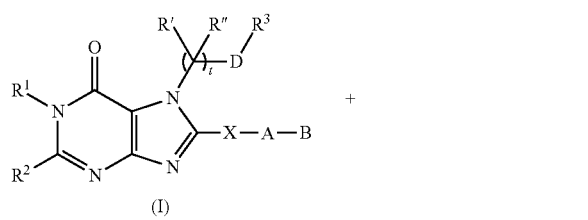

where $R^1$, $R^2$, R', R", $R^3$, D, t, X, A and B are as defined above.
Yet another embodiment of the present disclosure relates to a process for the preparation of a compound of formula (I) or formula (II), or its tautomers, polymorphs, stereoisomers or a pharmaceutically acceptable salts thereof, said process comprising: reacting compound of formula (1f)

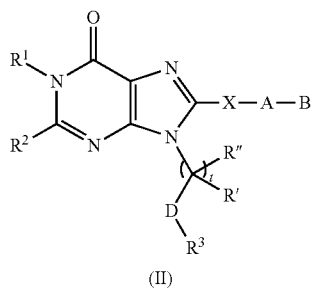

with compound of formula (1I)

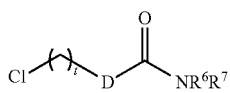

to obtain compound of formula (I) and formula (II)

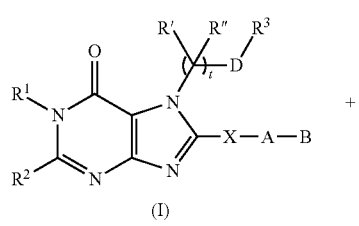

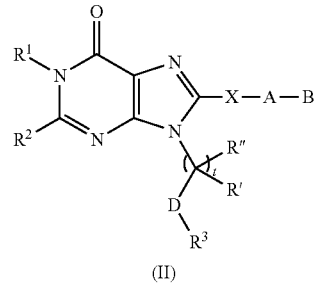

where $R^1$, $R^2$, R', R", $R^3$, D, t, X, A and B are as defined above.

The compounds of formula I and II may be prepared as outlined in the Scheme 1 and 3 below:

Scheme-1:

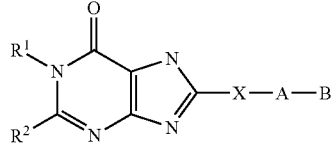

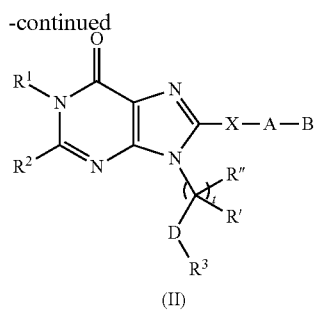

(II)

The compound of formula (1a), wherein all symbols are defined earlier is prepared by means well known in the art (US2008/0194593).

A compound of formula (1a) is reacted with a carboxylic acid of formula (1b), (which is available commercially or prepared by means well known in the art), wherein all symbols are defined earlier, to yield a compound of formula (1c). The reaction is carried out using a suitable coupling agent such as EDCI, DCC, HBTU, HATU and the like in a protic solvent such as methanol, ethanol, propanol and the like or an aprotic solvent such as DMF, $CH_2Cl_2$ and the like at a temperature in the range of 20-30° C. for 4 to 16 hours to provide compound of formula (1c).

The compound (1c) is also prepared from reaction of (1a) with an acid halide of (1b). The reaction is carried out in a solvent such as acetonitrile, THF and the like, in the presence of tertiary base such as triethyl amine. The reaction temperature range from 0° C. to reflux temperature of the solvent(s) used. The reaction time range from 4 to 48 hours. After completion of reaction the product of formula (1c) is isolated by conventional methods.

The compound of formula (1c) is cyclised to obtain compound of formula (1d) by a cyclization reaction. The reaction is carried out in the presence of hexamethyldisilazane and ammonium sulphate for about 24-48 hours at reflux temperature.

The compounds of formula (1d) is converted to compounds of formula (1e) by treatment with dehydrating agent such as $POCl_3$ or in combination with $POCl_3$ and $PCl_5$, at reflux temperature for about 24 hours. Alternatively (1c) is converted into compounds of formula (1e) by reaction with dehydiatin agent such as $POCl_3$ or in combination with $POCl_3$-$PCl_5$, at reflux temperature for about 24 hours.

Dehalogenation of the compounds of formula (1e) is carried out using hydrogenation or by transfer hydrogenation in the presence of a suitable catalyst such as Pd/C, $Pd(OH)_2/C$ and the like. In general, the compound of formula (1e) is dissolved in DMF and treated with ammonium formate in presence of 10% Pd/C and water at a temperature of about 60-65° C. The reaction time range from 1 to 18 hours. After completion of reaction, the compounds of formula (1f) wherein $R^2$ is hydrogen and all other symbols are defined herein above is isolated by conventional methods.

Alternatively, compounds of formula (1e) is converted to compounds of formula (1f) by reacting with MCN (M is Na or K), $R^2$—$NH_2$, $R^2R^2NH$, $R^2$—$B(OH)_2$, $R^2MgBr$, $R^2ZnCl$, $R^2OH$ wherein $R^2$ is defined herein above, by methods well known in the art to provide compounds of formula (1f).

The compound of formula (1f) can be reacted with compound of formula (1g), where in L1 is a leaving group such as chlorine, bromine and the like, in presence of base such as $K_2CO_3$, $Cs_2CO_3$ or NaH in a polar solvent such as DMF, acetone to obtain compound of formula (I) and formula (II).

The reaction temperature range from 40-60° C. and the reaction time range from 4 to 24 hours. After completion of reaction, the desired products are isolated by conventional methods.

When $R^3$ is —$C(O)R^4$ where in $R^4$ is defined above or $R^4$ is heterocycle, the compound of formula (1g, $R^4C(O)OCH_2L1$) is either commercially available or can be prepared by known methods from starting materials either known in the art or prepared by methods well known in the art (U.S. Pat. No. 7,625,881).

Scheme-2:

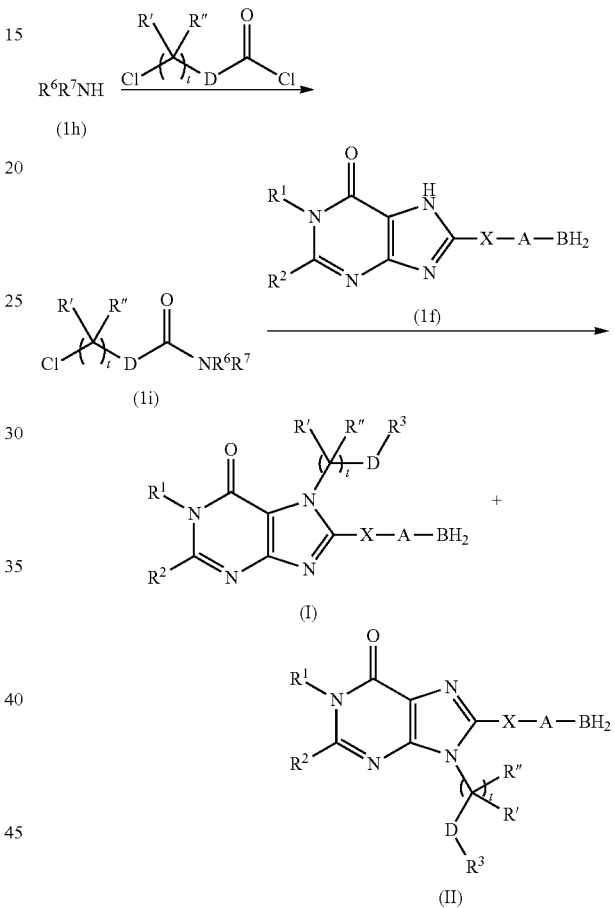

The compound of formula (1h) and (1i) are either commercially available or can be prepared by methods well known in the art. In general the compound of formula (1h) is reacted with Cl—$(CR'R'')_t$-D-COCl in presence base such as $Et_3N$ and the like in an inert solvent such as dichloromethane or polar solvent such as DMF to obtain compound of formula (II). The reaction temperature range from 0-20° C. and the reaction time range from 4 to 24 hours. After completion of reaction, the desired product (1i) is isolated by conventional method. The compound of formula (1i) is reacted with compound of formula (1f) in presence of base such as $K_2CO_3$, $Cs_2CO_3$ and the like in a polar solvent such as DMF, acetone. The reaction temperature ranges from 40-60° C. and the reaction time ranges from 4 to 24 hours. After completion of reaction, the desired products of formula (I) and (II) wherein R' and R" are hydrogen, D is O, $R^3$ is —$C(O)R^4$, $R^4$ is —$NR^6R^7$ and all other symbols are defined herein above, is isolated by conventional method.

Scheme-3:

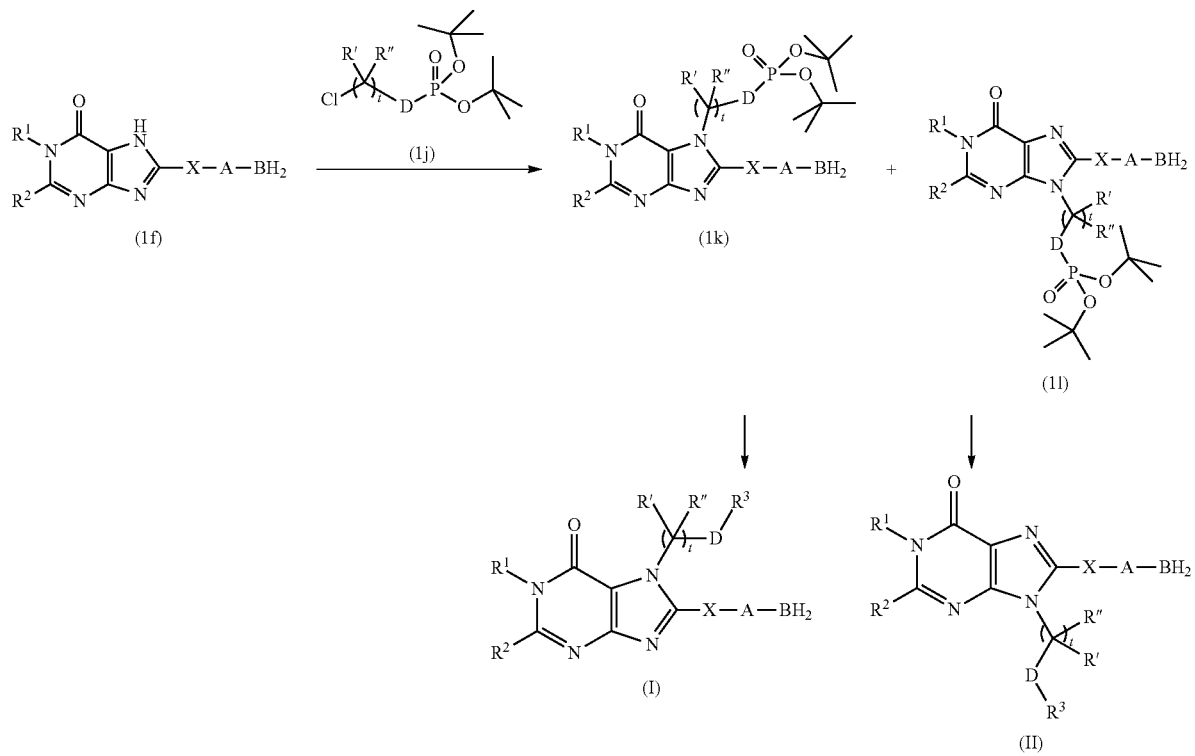

The compound of formula (1j) which is either commercially available or can be prepared by methods well known in the art. (Tetrahedron Lett. 43, 2002, 3793-3794; U.S. Pat. No. 7,625,881). The compound of formula (1f) is reacted with compound of formula (1j) in a polar solvent such as DMF, acetone and the like, in presence of base such as $K_2CO_3$, $Cs_2CO_3$ and the like to obtain compound of formula (1k) and (1l). In this reaction NaI is used as an additive. The reaction temperature range from 40-60° C. and the reaction time ranges from 4 to 24 hours. After completion of reaction, the desired products (1k and 1l) are separated and isolated by column chromatography. The product of formula (1k) and (1l) are deprotected conventionally with strong acid such as TFA or alternatively a weak acid such as formic acid, in an inert solvent such as DCM. The reaction temperature range from 0-30° C. and the reaction time range from 4 to 24 hours. After completion of reaction, the desired products of formula I and II wherein D is O, $R^3$ is —$P(O)(OR^5)_2$ and $R^5$ is hydroxy and all other symbols are defined herein above, is isolated by conventional methods.

Wherever desired or necessary, in any of the above mentioned processes, functional groups is transformed to different functional groups such as an ester function being converted to an acid, amide, hydroxymethyl, keto, aldehyde as well as an ester. The said conversions is carried out using reagents and conditjons well documented in the literature.

Wherever desired or necessary, in any of the above mentioned processes, any of the compounds of formula (I) or (II) is converted into a pharmaceutically acceptable salt or vice versa or converting one salt form into another pharmaceutically acceptable salt form.

According to an embodiment, the compounds of the present disclosure are pro-drugs of adenosine $A_{2B}$ receptor antagonists. Thus, the present disclosure provides a method for the modulation of adenosine $A_{2B}$ receptor activity in mammals which method comprises administering to a mammal in need thereof a therapeutically effective amount of compound of formula (I) or (II) or its tautomers, polymorphs, stereoisomers, solvates or a pharmaceutically acceptable salts thereof.

As used throughout the specification and in the claims, the term "treatment" embraces all the different forms or modes of treatment as known to those of the pertinent art and in particular includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, sheep, monkeys, rabbits, mice and laboratory animals The preferred mammals are humans.

An embodiment of the present disclosure relates to a pharmaceutical composition comprising, as an active ingredient, at least one compound of formula (I) or formula (II), or its tautomers, polymorphs, stereoisomers, solvates or a pharmaceutically acceptable salts thereof, together with one or more phmtnaceutically acceptable carriers or excipients.

The present disclosure further provides pharmaceutical compositions comprising a therapeutically effective amount of a compound of the present disclosure, alone or in combination with one or more pharmaceutically acceptable carriers.

The pharmaceutical compositions according to the present disclosure are those suitable for enteral, such as oral or rectal, transdermal and parenteral administration to mammals, including man, for the treatment of conditions mediated by the adenosine $A_{2B}$ receptor. Such conditions include, but are not limited to, asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders including inflammatory bowel disease, sickle cell disease, and/or autoimmune diseases.

Generally, the concentration of the compound(s) of the present disclosure in a liquid composition, such as a lotion, will be from about 0.01-about 25 wt %, preferably from about 0.1-about 10 wt %. The concentration in a semi-solid or a solid composition such as a gel or a powder will be about 0.1-about 5 wt %, preferably about 0.5-about 25 wt %.

The amount of a compound of the present disclosure required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.001 mg/kg/day to about 20 mg/kg/day For example, a dosage may be from about 0.002 mg/kg to about 10 mg/kg of body weight per day, from about 0.01 mg/kg/day to about 1 mg/kg/day, and from about 0.1 mg/kg/day to about 5 mg/kg/day.

The compound is conveniently administered in unit dosage form, e.g, containing 5 to 1000 μg, about 10 to about 750 μg, about 50 to about 500 μg of active ingredient per unit dosage form.

The desired dose may conveniently be presented in a single dose or as divided doses administered at appropriate intervals, for example, as two, three, four or more sub-doses per day. The sub-dose itself may be further divided, e g, into a number of discrete loosely spaced administrations; such as multiple inhalations from an insufflator or by application of a plurality of drops into the eye Dosages above or below the range cited herein above are within the scope of the present disclosure and may be administered to the individual patient if desired and necessary.

Accordingly, in various embodiments, the present disclosure provides pharmaceutical compositions as described above for the treatment of conditions mediated by adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders including inflammatory bowel disease, sickle cell disease, and/or autoimmune diseases.

An embodiment of the present disclosure also relates to a pharmaceutical composition comprising a compound of formula (I) or formula (II) or its tautomers, polymorphs, stereoisomers, solvates or a pharmaceutically acceptable salts thereof, in combination with one or more therapeutically active agents.

In various embodiments, the present disclosure provides pharmaceutical compositions comprising a therapeutically effective amount of a compound of the disclosure in combination with a therapeutically effective amount of another therapeutic agent, preferably selected from anti-inflammatory agents, anti-diabetic agents, anti-hypertensive agents and anti-dyslipidemic agents.

According to an embodiment, the pharmaceutical compositions may contain a therapeutically effective amount of a compound of the disclosure as defined above, either alone or in a combination with another therapeutic agent, e.g., each at an effective therapeutic dose as reported in the art. Such therapeutic agents include: a) anti-inflammatory agents, such as anticholinergic or antimuscarinic agents; steroids; $LTB_4$ (leukotriene $B_4$) antagonists; dopamine receptor agonists; $PDE_4$ (phosphodiesterase 4) inhibitors; and beta-2 adrenergic receptor agonists; b) anti-diabetic agents, such as insulin, insulin derivatives and mimetics; insulin secretagogues; insulinotropic sulfonylurea receptor ligands; thiazolidone derivatives; GSK3 (glycogen synthase kinase-3) inhibitors; sodium-dependent glucose co-transporter inhibitors; glycogen phosphorylase A inhibitors; biguanides; alpha-glucosidase inhibitors; GLP-1 (glucagon like peptide-1), GLP-1 analogs and GLP-1 mimetics; modulators of PPARs (peroxisome proliferator-activated receectors); DPPIV (dipeptidyl peptidase IV) inhibitors; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products); c) anti-hypertensive agents, such as loop diuretics; angiotensin converting enzyme (ACE) inhibitors; inhibitors of the Na-K-ATPase membrane pump such as digoxin; neutralendopeptidase (NEP) inhibitors; ACE/NEP inhibitors; angiotensin II antagonists; renin inhibitors; β-adrenergic receptor blockers; inotropic agents; calcium channel blockers; aldosterone receptor antagonists; and aldosterone synthase inhibitors; and d) anti-dyslipidemic agents such as 3-hydroxy-3-methyl-glutaryl coenzyme A (HMG-CoA) reductase inhibitors; HDL increasing compounds such as cholesterol ester transfer protein (CETP) inhibitors; squalene synthase inhibitors; FXR (farnesoid X receptor) and LXR (liver X receptor) ligands; cholestyramine; fibrates; nicotinic acid; and aspirin.

Pharmaceutical Compositions

The compounds of Formula I and II are usually administered in the form of pharmaceutical compositions. This disclosure therefore provides pharmaceutical compositions that contain, as the active ingredient, one or more of the compounds of Formula I and II, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I and II may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17 .sup.th Ed. (1985) and "Modern Pharmaceutics", Marcel DAker, Inc. 3 .sup.rd Ed. (G. S. Banker & C. T. Rhodes, Eds.).

Administration

The compounds of Formula I and II may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The following examples are included to demonstrate preferred embodiments of the present disclosure. It should be appreciated by those of skill in the art that the techniques disclosed in the examples which follow represent techniques discovered by the inventor to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

EXAMPLES

The present disclosure is further illustrated by the following examples which in no way should be construed as being further limiting. One skilled in the art will readily appreciate that the specific methods and results described are merely illustrative. Structures of the intermediates as well as the final compounds were confirmed by nuclear magnetic resonance spectra for proton ($^1$H NMR) and LCMS.

Example 1

Phosphoric acid mono-{2-cyano-6-oxo-1-propyl-8-[1-(3-trifluoromethyl-benzyl)-1H-pyrazol-4-yl]-1,6-dihydro-purin-7-ylmethyl}ester

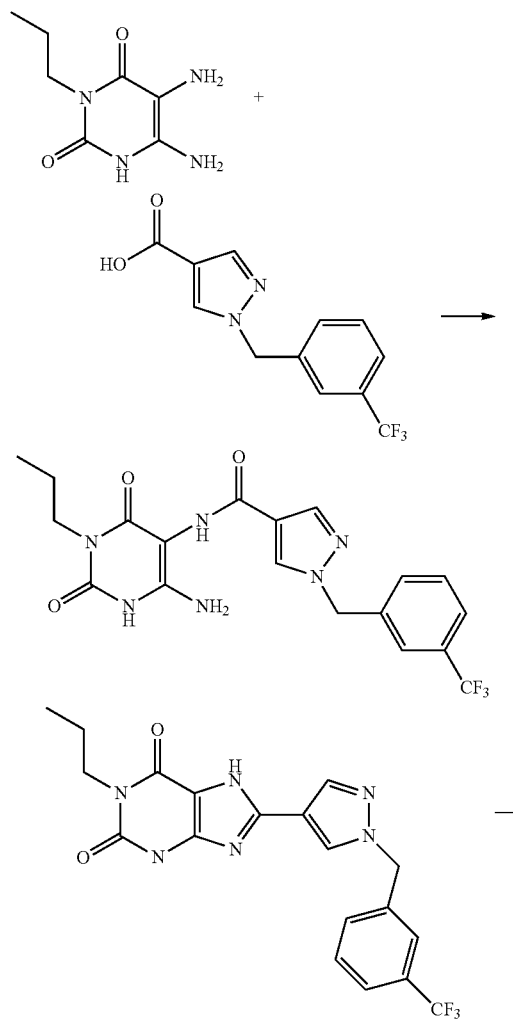

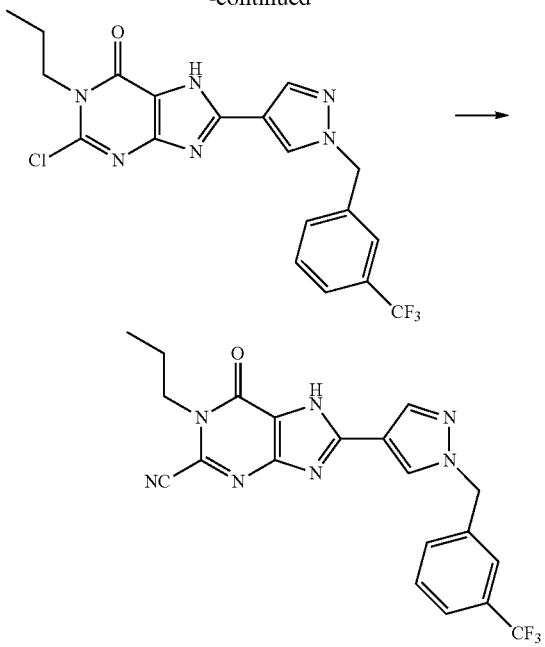

Step I: Synthesis of 1-(3-Trifluoromethyl-benzyl)-1H-pyrazole-4-carboxylic acid (6-amino-2,4-dioxo-3-propyl-1,2,3,4-tetrahydro-pyrimidin-5-yl)-amide A mixture of 5,6-diamino-3-propyl-1H-pyrimidine-2,4-dione (4.25 g, 0.023 mol), 1-(3-Trifluoromethyl-benzyl)-1H-pyrazole-4-carboxylic acid (6.23 g, 0.023 mol), prepared by conventional methods starting from pyrazole-4-carboxylic ester, in methanol (50 ml) were cooled to 0° C. and added EDCI.HCl (8.82 g, 0.046 mol). The reaction mixture was stirred at 25° C. for 6 h and the organic volatiles were evaporated. To this residue water (50 ml) was added and the precipitate was filtered off, and washed with cold water (50 ml) to obtain 1-(3-Trifluoromethyl-benzyl)-1H-pyrazole-4-carboxylic acid (6-amino-2,4-dioxo-3-propyl-1,2,3,4-tetrahydro-pyrimidin-5-yl)-amide (7.2 g, 72%) as a pale yellow solid.

$^1$HNMR (400 MHz, DMSO d6): δ 0.82 (t, J=7.6 Hz, 3H); 1.46-1.51 (m, 2H); 3.64 (t, J=7.2 Hz, 2H); 5.49 (s, 2H); 6.01 (s, 2H); 7.55-7.63 (m, 2H); 7.68-7.72 (m, 2H); 7.99 (s, 1H); 8.37 (s, 1H); 8.55 (s, 1H); 10.42 (s, 1H).

Step II: Preparation of 1-Propyl-8-[1-(3-trifluoromethyl-benzyl)-1H-pyrazol-4-yl]-3,7-dihydro-purine-2,6-dione A mixture of 1-(3-Trifluoromethyl-benzyl)-1H-pyrazole-4-carboxylic acid (6-amino-2,4-dioxo-3-propyl-1,2,3,4-tetrahydro-pyrimidin-5-yl)-amide (30 g, 0.068 mol), $P_2O_5$ (34.0 g, 0.240.8 mol) and DMF (300 ml) were heated at 100° C. for 30 minutes. The reaction mixture was cooled to 20-25° C. The reaction mixture was slowly poured into water (1.5 L) with vigorous stirring. Solid material separated was filtered off, and washed with water (200 ml) to obtain 1-Propyl-8-[1-(3-trifluoromethyl-benzyl)-1H-pyrazol-4-yl]-3,7-dihydro-purine-2,6-dione (25 g, 88%) as a pale yellow solid.

$^1$HNMR (400 MHz, DMSO d6): δ 0.87 (t, J=7.2 Hz, 3H); 1.53-1.60 (m, 2H); 3.98 (t, J=7.211z, 2H); 5.53 (s, 2H); 7.57-7.64 (m, 2H); 7.69-7.71 (m, 2H); 8.08 (s, 1H); 8.47 (s, 1H); 11.83 (s, 1H); 13.39 (s, 1H)

Step III: Preparation of 2-Chloro-1-propyl-8-[1-(3-trifluoromethyl-benzyl)-1H-pyrazol-4-yl]-1,7-dihydro-purin-6-one A mixture of 1-Propyl-8-[1-(3-trifluoromethyl-benzyl)-1H-pyrazol-4-yl]-3,7-dihydro-purine-2,6-dione (7.2 g, 0.017 mol), NH$_4$Cl (4.54 g, 0.085 mol) and POCl$_3$ (220 ml) were heated at 120-125° C. for 72 h. Reaction mixture was cooled to 20-25° C. It was then concentrated under vacuum and quenched with cold water slowly and solid material was separated. It was filtered off and washed with water. The solid material was dried under vacuum. The crude product was purified by column chromatography using silica gel (230-400 mesh) and 0.5 to 4% methanol in chloroform as an eluent to obtain 2-Chloro-1-propyl-8-[1-(3-trifluoromethyl-benzyl)-1H-pyrazol-4-yl]-1,7-dihydro-purin-6-one (4.2 g, 58%) as a pale yellow solid.

$^1$HNMR (400 MHz, CD$_3$OD): δ 1.02 (t, J=7.2 Hz, 3H); 1.78-1.84 (m, 2H); 4.29 (t, J=7.6 Hz, 2H); 5.52 (s, 2H); 7.56-7.57 (m, 2H); 7.63 (m, 2H); 8.12 (s, 1H); 8.35 (s, 1H)

Step IV: Preparation of 6-Oxo-1-propyl-8-[1-(3-trifluoromethyl-benzyl)-1H-pyrazol-4-yl]-6,7-dihydro-1H-purine-2-carbonitrile A mixture of 2-Chloro-1-propyl-8-[1-(3-trifluoromethyl-benzyl)-1H-pyrazol-4-yl]-1,7-dihydro-purin-6-one (0.1 g, 0.23 mmol), NaCN (0.016 g, 0.35 mmol), NaI (0.069 g, 0.46 mmol) and DMF (2 ml) were stirred for 48 h at 65-70° C. Reaction mixture was cooled to 20-25° C. and water was added. Solid material was separated. It was filtered off and washed with water. The product was dried under vacuum to obtain 6-Oxo-1-propyl-8-[1-(3-trifluoromethyl-benzyl)-1H-pyrazol-4-yl]-6,7-dihydro-1H-purine-2-carbonitrile (0.075 g, 77%) as an off white solid.

$^1$HNMR (400 MHz, DMSO d6): δ 0.97 (t, J=7.6 Hz, 3H); 1.71-1.77 (m, 2H); 4.12 (t, J=7.6 Hz, 2H); 5.51 (s, 2H); 7.57-7.67 (m, 4H); 8.14 (s, 1H); 8.55 (s, 1H); 14.01 (bs, 1H)

Preparation of phosphoric acid di-tert-butyl ester chloromethyl ester

Step I: Phosphoric acid di-tert-butyl ester

A mixture of di-tert-butylphosphite (5 g, 0.026 mol), NaHCO$_3$ (3.71 g, 0.044 mol) and water (50 ml) were taken and cooled to 0-(−5, ° C. KMnO$_4$ (6.18 g, 0.039 mol) was added to the reaction mixture in portion wise over a period of 30 minutes at that temperature. The reaction mixture was allowed to warm to 20-25° C. and stirred for 1.5 hours at that temperature. To this reaction mixture activated charcoal (25 g) was added and stirred at 55-60° C. for 1 hour. The reaction mixture was cooled to room temperature and filtered off and washed with water (200 ml). The filtrate was concentrated to half of its volume and cooled to 0° C. It was then acidified with con. HCl (pH~1-2) to obtain solid. The solid material was filtered off, washed with ice cold water and dried under vacuum to obtain Phosphoric acid di-tert-butyl ester as white solid (3.44 g, 63%).

Step II. Phosphoric acid di-tert-butyl ester chloromethyl ester

A mixture of Phosphoric acid di-tert-butyl ester (1 g, 0.0048 mol), NaHCO$_3$ (0.806 g, 0.0096 mol), tetra butyl ammonium hydrogen sulphate (0.163 g, 0.00048 mol), water (40 ml) and DCM (25 ml) were taken. The mixture was cooled to 0° C. and stirred at that temperature for 20 minutes. Chloromethyl chlorosulphate, (0.943 g, 0.0057 mol) in DCM (15 ml) was added to it at 0° C. The reaction mixture allowed to warm to room temperature and stirred for 18 hours. The organic layer was separated and aqueous layer was extracted with DCM (30 ml). The organic layer was washed with brine (60 ml) solution and dried over Na$_2$SO$_4$. The organic layer was evaporated to obtain Phosphoric acid di-tert-butyl ester chloromethyl ester as colorless oil (0.79 g, 64%).

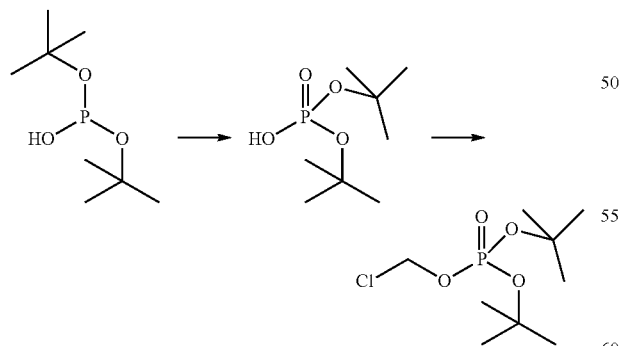

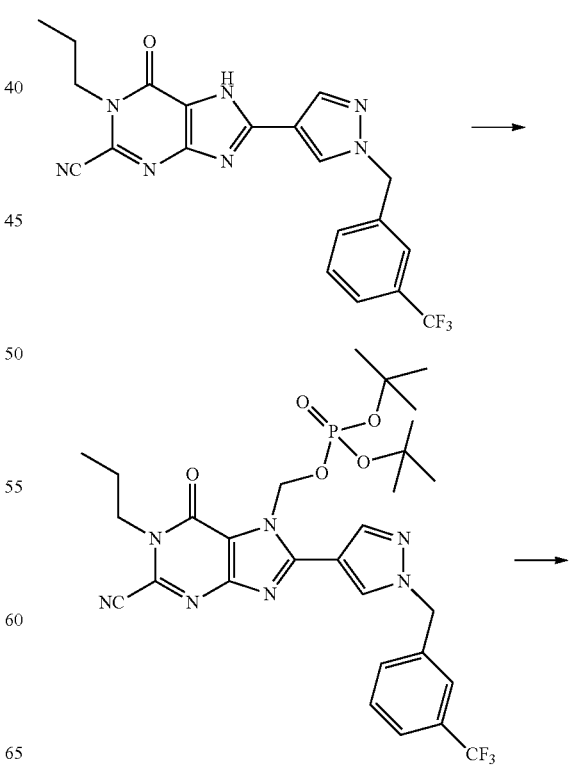

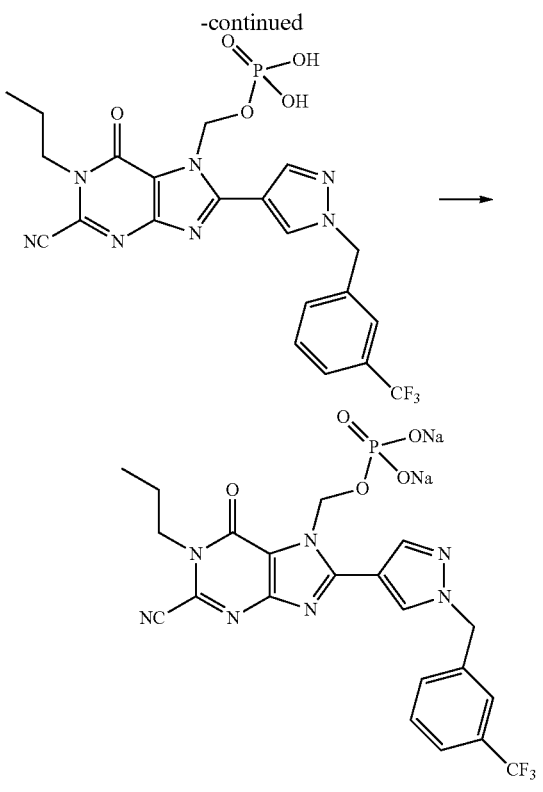

Step I: Phosphoric acid di-tert-butyl ester 2-cyano-6-oxo-1-propyl-8-[1-(3-trifluoromethyl-benzyl)-1H-pyrazol-4-yl]-1,6-dihydro-purin-7-ylmethyl ester A mixture of 6-Oxo-1-propyl-8-[1-(3-trifluoromethyl-benzyl)-1H-pyrazol-4-yl]-6,7-dihydro-1H-purine-2-carbonitrile (0.5 g, 0.0012 mol), K₂CO₃ (0.485 g, 0.0036 mol) and acetone (10 ml) were taken and stirred for 20 minutes at room temperature. NaI (0.702 g, 0.0047 mol) was added and then Phosphoric acid di-tert-butyl ester chloromethyl ester (0.619 g, 0.0024 mol in 2 ml acetone) was added to the reaction mixture drop wise. The reaction mixture was heated at 45° C. for 16 h. The reaction mixture was filtered through celite and washed with acetone. The organic layer was concentrated and the residue was taken in ethyl acetate (30 ml) and saturated NaHCO₃ solution (20 ml). The organic layer was separated and washed with saturated sodium thiosulphate solution (20 ml). The organic layer was washed with 0.5 N HCl solution (20 ml) and brine solution (20 ml). The organic layer was dried over sodium sulphate and evaporated to obtain brown colored mass. The crude product, which is a mixture of N7 and N9 isomers was purified by column chromatography (230-400 mesh silica gel and it was first treated with 5% triethyl amine in hexane) using 5-20% acetone in hexane (with 0.5 to 1% triethyl amine) as an eluent to obtain N7 isomer (0.34 g, 45%) and N9 isomer (0.11 g, 14%)

Phosphoric acid di-tert-butyl ester 2-cyano-6-oxo-1-propyl-8-[1-(3-trifluoromethyl-benzyl)-1H-pyrazol-4-yl]-1,6-dihydro-purin-7-ylmethyl ester (N-7-isomer)

¹H NMR (400 MHz, DMSO d6): δ 0.95 J=8 Hz, 3H); 125 (s, 18H); 1.75-1.80 (m, 2H); 4.18 (t, J=7.2 Hz, 2H); 5.58 (s, 2H); 6.34 (d, J=8.8 Hz, 2H); 7.61-7.63 (m, 2H); 7.70-7.73 (m, 2H); 8.19 (s, 1H); 8.75 (s, 1H)

Phosphoric acid di-tert-butyl ester 2-cyano-8-[1-(3-trifluoromethyl-benzyl)-1H-pyrazol-4-yl]-6-oxo-1-propyl-1,6-dihydro-purin-9-ylmethyl ester (N9-isomer)

¹H NMR (400 MHz, DMSO d6): δ 0.94 (t, J=8 Hz, 3H); 125 (s, 18 H); 1.74-1.78 (m, 2H); 4.21 (t, J=7.2 Hz, 2H); 5.59 (s, 2H); 6.05 (d, J=10.8 Hz, 2H); 7.62-7.63 (m, 2H); 7.69-7.71 (m, 2H); 8.16 (s, 1H); 8.71 (s, 1H)

Step II: Phosphoric acid mono-{2-cyano-6-oxo-1-propyl-8-[1-(3-trifluoromethyl-benzyl)-1H-pyrazol-4-yl]-1,6-dihydro-purin-7-ylmethyl}ester (N7-isomer)

The above product, N7 isomer (0.34 g, 0.52 mmol) was dissolved in DCM (20 ml) and TFA (0.29 ml, 4.2 mmol) was added to it. The reaction mixture was stirred at room temperature for 7 hours. The organic volatiles were evaporated and the residue was stirred with pentane: diethyl ether (3:1, 10 ml) and the solid material obtained was filtered off and washed with 10% diethyl ether in pentane (10 ml) to obtain Phosphoric acid mono-{2-cyano-6-oxo-1-propyl-8-[1-(3-trifluoromethyl-benzyl)-1H-pyrazol-4-yl]-1,6-dihydro-purin-7-ylmethyl}ester (0.239 g, 85%) as an off white solid.

(400 MHz, DMSO d6): δ 0.96 (t, J=7.6 Hz, 3H); 1.75-1.81 (m, 2H); 4.16 (t, J=7.2 Hz, 2H); 5.58 (s, 2H); 6.23 (d, J=6 Hz, 2H); 7.61-7.63 (m, 2H); 7.69-7.75 (m, 2H); 8.22 (s, 1H); 8.80 (s, 1H); (M+1): 538.2

Phosphoric acid mono-{2-cyano-6-oxo-1-propyl-8-[1-(3-trifluoromethyl-benzyl)-1H-pyrazol-4-yl]-1,6-dihydro-purin-9-ylmethyl}ester (N9-isomer, 28%)

(400 MHz, DMSO d6): δ 0.93 (t, J=7.6 Hz, 3H); 1.72-1.80 (m, 2H); 4.16 (t, J=7.2 Hz, 2H); 5.54 (s, 2H); 5.95 (d, J=6 Hz, 2H); 7.59-7.60 (m, 2H); 7.67-7.73 (m, 2H); 8.17 (s, 1H); 8.72 (s, 1H).

Step III: Phosphoric acid mono-{2-cyano-6-oxo-1-propyl-8-[1-(3-trifluoromethyl-benzyl)-1H-pyrazol-4-yl]-1,6-dihydro-purin-7-ylmethyl}ester di sodium salt The above product (0.239 g, 0.44 mmol) and water (25 ml) were taken. To the suspension formed, NaHCO₃ solution (0.112 g, 1.3 mmol in 20 ml water) was added. The reaction mixture was stirred at room temperature for 1.5 h and the solid material obtained was filtered off. The clear solution was passed through reverse phase column chromatography (LCMS). The fraction obtained was evaporated. It was lyophilized to obtain pure Phosphoric acid mono-{2-cyano-6-oxo-1-propyl-8-[1-(3-trifluoromethyl-benzyl)-1H-pyrazol-4-yl]-1,6-dihydro-purin-7-ylmethyl}ester di sodium salt (0.208 g; 80%) as an off white solid.

¹H NMR: (400 MHz, D₂O): δ 0.97 (t, J=7.6 Hz, 3H); 1.80-1.86 (m, 2H); 4.28 (t, J=7.6 Hz, 2H); 5.53 (s, 2H); 6.04 (d, J=3.2 Hz, 2H); 7.52-7.53 (m, 2H); 7.62-7.64 (m, 2H); 8.22 (s, 1H); 8.74 (s, 1H)

³¹P NMR: (400 MHz, D₂O): δ 0.447

Example 2

Phosphoric acid mono-{2-cyano-6-oxo-1-propyl-8-[1-(3-trifluoromethyl-benzyl)-1H-pyrazol-4-yl]-1,6-dihydro-purin-9-ylmethyl}ester di sodium salt (N9-isomer, 65%)

¹H NMR: (400 MHz, D₂O): δ 0.83 (t, J=7.6 Hz, 3H); 1.67-1.73 (m, 2H); 4.16 (t, J=7.6 Hz, 2H); 5.40 (s, 2H); 5.72 (bs, 2H); 7.39-7.40 (m, 2H); 7.48-7.54 (m, 2H); 8.08 (s, 1H); 8.52 (s, 1H) Examples 3 and 4 were prepared in an aDalogous manner of Examples 1 and 2.

| Example No. | Structure | IUPAC Name | NMR (400 MHz, DMSO d6) |
|---|---|---|---|
| 3 | 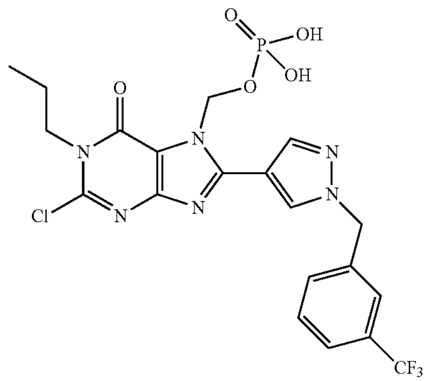 [SMILES: CCCn1c(Cl)nc2nc(-c3cnn(Cc4cccc(C(F)(F)F)c4)c3)n(COP(=O)(O)O)c2c1=O] | Phosphoric acid mono-{2-chloro-6-oxo-1-propyl-8-[1-(3-trifluoromethyl-benzyl)-1H-pyrazol-4-yl]-1,6-dihydro-purin-7-ylmethyl}ester | δ 0.94 (t, J = 7.2 Hz, 3H); 1.61-1.72 (m, 2H); 4.11 (t, J = 7.6 Hz, 2H); 5.50 (s, 2H); 5.98 (s, 2H); 7.56-7.72 (m, 4H); 8.25 (s, 1H); 9.03 (s, 1H) |
| 4 | 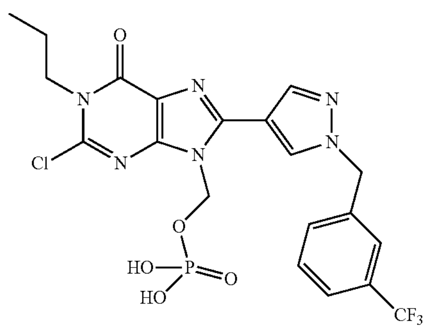 [SMILES: CCCn1c(Cl)nc2c(nc(-c3cnn(Cc4cccc(C(F)(F)F)c4)c3)n2COP(=O)(O)O)c1=O] | Phosphoric acid mono-{2-chloro-6-oxo-1-propyl-8-[1-(3-trifluoromethyl-benzyl)-1H-pyrazol-4-yl]-1,6-dihydro-purin-9-ylmethyl}ester | δ 0.93 (t, J = 7.2 Hz, 3H); 1.68-1.70 (m, 2H); 4.15 (t, J = 7.6 Hz, 2H); 5.49 (s, 2H); 5.64 (s, 2H); 7.58-7.70 (m, 4H); 8.19 (s, 1H); 8.98 (s, 1H) |

Example 5 and 6

2,2-Dimethyl-propionic acid 6-oxo-1-propyl-8-[1-(3-trifluoromethyl-benzyl)-1H-pyrazol-4-yl]-1,6-dihydro-purin-7-ylmethyl ester and 2,2-Dimethyl-propionic acid 6-oxo-1-propyl-8-[1-(3-trifluoromethyl-benzyl)-1H-pyrazol-4-yl]-1,6-dihydro-purin-9-ylmethyl ester

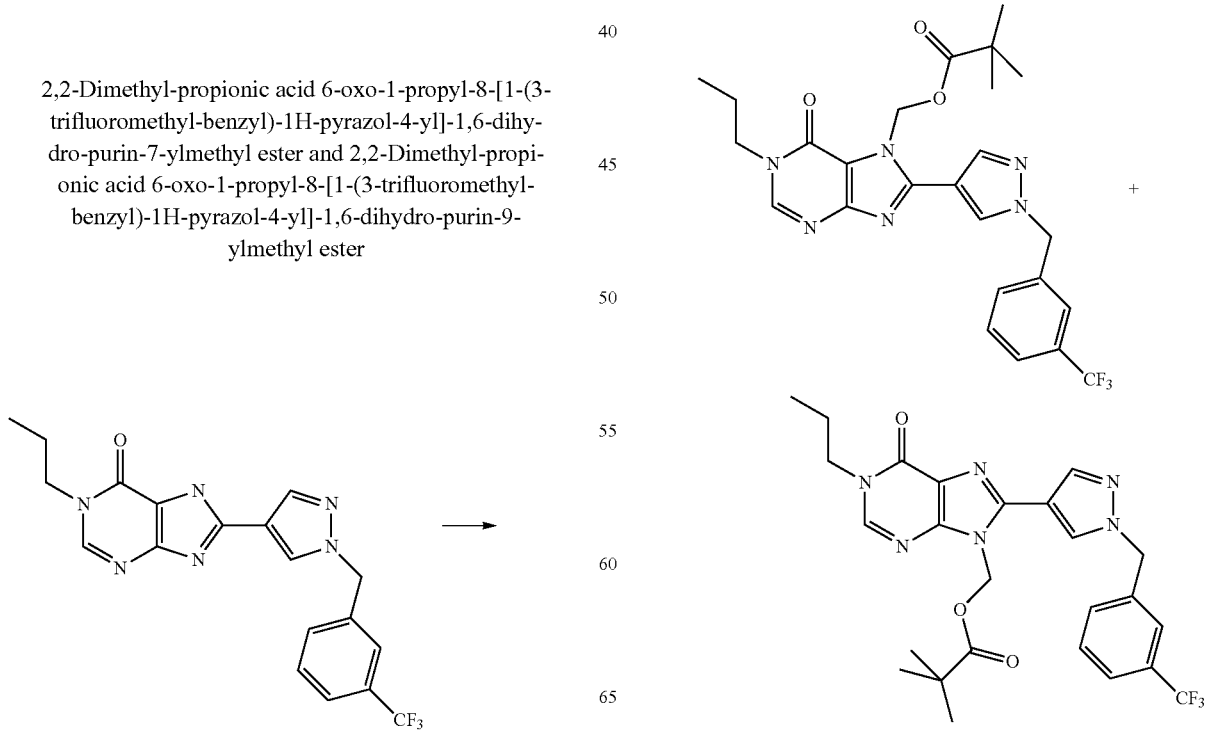

Example 5

2,2-Dimethyl-propionic acid 6-oxo-1-propyl-8-[1-(3-trifluoromethyl-benzyl)-1H-pyrazol-4-yl]-1,6-dihydro-purin-7-ylmethyl ester To a solution of 2-Chloro-1-propyl-8-[1-(3-trifluoromethyl-benzyl)-1H-pyrazol-4-yl]-1,7-dihydro-purin-6-one (0.35 gm, 0.87 mmol) in DMF (5 ml) K2CO3 (0.360 gm, 2.59 mmol) was added under nitrogen atmosphere. To this reaction mixture Chloromethyl pivalate (0.395 gm, 2.62 mmol) was added at room temperature. It was stirred at 50° C. for 24 hrs. Reaction mixture was filtered and DMF was evaporated. Residue obtained was purified by LCMS to obtain above two isomers, Example 5 and Example 6.

$^1$NMR (400 MHz, DMSO-d6): δ 0.87 (t, J=7.2 Hz, 3H); 1.00 (s, 9H); 1.66-1.72 (m, 2H); 3.96 (t, J=7.6 Hz, 2H); 5.57 (s, 2H); 6.47 (s, 2H); 7.61-7.63 (m, 2H); 7.69-7.70 (m, 2H); 8.07 (s, 1H); 8.37 (s, 1H); 8.60 (s, 1H).

Example 6

2,2-Dimethyl-propionic acid 6-oxo-1-propyl-8-[1-(3-trifluoromethyl-benzyl)-1H-pyrazol-4-yl]-1,6-dihydro-purin-9-ylmethyl ester $^1$NMR (400 MHz, DMSO-d6): δ 0.88 (t, J=7.2 Hz, 3H); 1.00 (s, 9H); 1.66-1.72 (m, 2H); 3.97 (t, J=7.2 Hz, 2H); 5.56 (s, 2H), 6.23 (s, 2H); 7.61-7.62 (m, 2H); 7.69-7.70 (m, 2H); 8.06 (s, 1H); 8.44 (s, 1H); 8.56 (s, 1H).

Examples 7-10 were prepared in an analogous manner of Examples 5 and 6.

| Example No. | Structure | IUPAC Name | NMR (400 MHz, DMSO d6) |
|---|---|---|---|
| 7 | 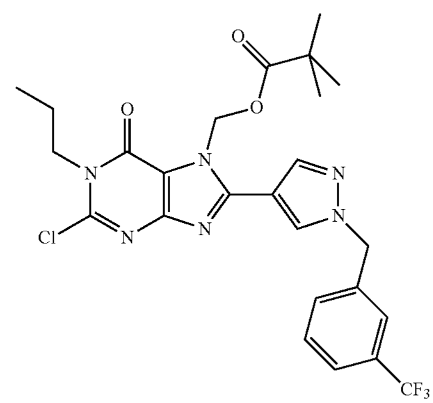 [SMILES: CCCn1c(Cl)nc2nc(-c3cnn(Cc4cccc(C(F)(F)F)c4)c3)n(COC(=O)C(C)(C)C)c2c1=O] | 2,2-Dimethyl-propionic acid 2-chloro-6-oxo-1-propyl-8-[1-(3-trifluoromethyl-benzyl)-1H-pyrazol-4-yl]-1,6-dihydro-purin-7-ylmethyl ester | δ 0.93 (t, J = 7.2 Hz, 3H); 1.01 (s, 9H); 1.66-1.76 (m, 2H); 4.16 (t, J = 7.2 Hz, 2H); 5.58 (s, 2H); 6.44 (s, 2H); 7.60-7.63 (m, 2H); 7.69-7.71 (m, 2H); 8.08 (s, 1H); 8.64 (s, 1H) |
| 8 | 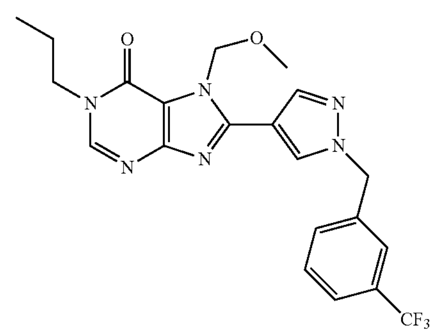 [SMILES: CCCn1cnc2nc(-c3cnn(Cc4cccc(C(F)(F)F)c4)c3)n(COC)c2c1=O] | 7-Methoxymethyl-1-propyl-8-[1-(3-trifluoromethyl-benzyl)-1H-pyrazol-4-yl]-1,7-dihydro-purin-6-one | δ 0.88 (t, J = 7.6 Hz, 3H); 1.67-1.73 (m, 2H); 3.3 (s, 3H); 3.98 (t, J = 7.2 Hz, 2H); 5.58 (s, 2H); 5.84 (s, 2H); 7.61-7.62 (m, 2H); 7.69-7.72 (m, 2H); 8.07 (s, 1H); 8.36 (s, 1H); 8.57 (s, 1H) |
| 9 | 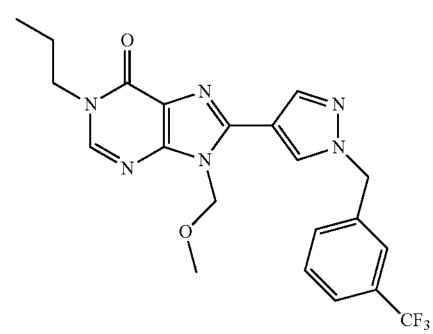 [SMILES: CCCn1cnc2c(nc(-c3cnn(Cc4cccc(C(F)(F)F)c4)c3)n2COC)c1=O] | 9-Methoxymethyl-1-propyl-8-[1-(3-trifluoromethyl-benzyl)-1H-pyrazol-4-yl]-1,9-dihydro-purin-6-one | δ 0.89 (t, J = 7.2 Hz, 3H); 1.67-1.73 (m, 2H); 3.31 (s, 3H); 3.98 (t, J = 6.8 Hz, 2H); 5.55 (s, 2H); 5.57 (s, 2H); 7.61-7.62 (m, 2H); 7.69-7.72 (m, 2H); 8.05 (s, 1H); 8.44 (s, 1H); 8.53 (s, 1H) |

| Example No. | Structure | IUPAC Name | NMR (400 MHz, DMSO d6) |
|---|---|---|---|
| 10 | 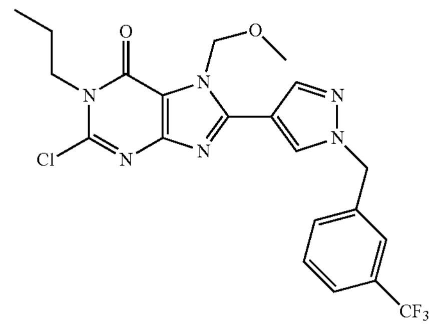 [SMILES: CCCn1c(Cl)nc2nc(-c3cnn(Cc4cccc(C(F)(F)F)c4)c3)n(COC)c2c1=O] | 2-Chloro-7-methoxymethyl-1-propyl-8-[1-(3-trifluoromethyl-benzyl)-1H-pyrazol-4-yl]-1,7-dihydro-purin-6-one | δ 0.93 (t, J = 7.2 Hz, 3H); 1.66-1.76 (m, 2H); 3.3 (s, 3H); 4.17 (t, J = 7.6 Hz, 2H); 5.58 (s, 2H); 5.81 (s, 2H); 7.60-7.63 (m, 2H); 7.68-7.70 (m, 1H); 7.74 (s, 1H); 8.08 (s, 1H); 8.60 (s, 1H) |

The list of examples synthesized following the general synthesis described above, but not limited to these, is provided below.

Phosphoric acid mono-{6-oxo-1-propyl-8-[1-(3-trifluoromethyl-benzyl)-1H-pyrazol-4-yl]-1,6-dihydro-purin-7-ylmethyl}ester;

(2-Dimethylamino-ethyl)-methyl-carbamic acid 6-oxo-1-propyl-8-[1-(3-trifluoromethyl-benzyl)-1H-pyrazol-4-yl]-1,6-dihydro-purin-7-ylmethyl ester;

(1-Ethyl-pyrrolidin-2-ylmethyl)-carbamic acid 6-oxo-1-propyl-8-[1-(3-trifluoromethyl-benzyl)-1H-pyrazol-4-yl]-1,6-dihydro-purin-7-ylmethyl ester;

Nicotinic acid 6-oxo-1-propyl-8-[1-(3-trifluoromethyl-benzyl)-1H-pyrazol-4-yl]-1,6-dihydro-purin-7-ylmethyl ester;

Acetic acid 6-oxo-1-propyl-8-[1-(3-trifluoromethyl-benzyl)-1H-pyrazol-4-yl]-1,6-dihydro-purin-7-ylmethyl ester;

Butyric acid 6-oxo-1-propyl-8-[1-(3-trifluoromethyl-benzyl)-1H-pyrazol-4-yl]-1,6-dihydro-purin-7-ylmethyl ester;

Butyric acid 2-chloro-6-oxo-1-propyl-8-[1-(3-trifluoromethyl-benzyl)-1H-pyrazol-4-yl]-1,6-dihydro-purin-7-ylmethyl ester;

Nicotinic acid 2-chloro-6-oxo-1-propyl-8-[1-(3-trifluoromethyl-benzyl)-1H-pyrazol-4-yl]-1,6-dihydro-purin-7-ylmethyl ester;

(2-Dimethylamino-ethyl)-methyl-carbamic acid 2-chloro-6-oxo-1-propyl-8-[1-(3-trifluoromethyl-benzyl)-1H-pyrazol-4-yl]-1,6-dihydro-purin-7-ylmethyl ester;

(2-Dimethylamino-ethyl)-methyl-carbamic acid 2-cyano-6-oxo-1-propyl-8-[1-(3-trifluoromethyl-benzyl)-1H-pyrazol-4-yl]-1,6-dihydro-purin-7-ylmethyl ester;

Butyric acid 2-cyano-6-oxo-1-propyl-8-[1-(3-trifluoromethyl-benzyl)-1H-pyrazol-4-yl]-1,6-dihydro-purin-7-ylmethyl ester;

2,2-Dimethyl-propionic acid 2-cyano-6-oxo-1-propyl-8-[1-(3-trifluoromethyl-benzyl)-1H-pyrazol-4-yl]-1,6-dihydro-purin-7-ylmethyl ester;

Nicotinic acid 2-cyano-6-oxo-1-propyl-8-[1-(3-trifluoromethyl-benzyl)-1H-pyrazol-4-yl]-1,6-dihydro-purin-7-ylmethyl ester;

4-Methyl-piperazine-1-carboxylic acid 2-cyano-6-oxo-1-propyl-8-[1-(3-trifluoromethyl-benzyl)-1H-pyrazol-4-yl]-1,6-dihydro-purin-7-ylmethyl ester;

1-{6-Oxo-7-phosphonooxymethyl-1-propyl-8-[1-(3-trifluoromethyl-benzyl)-1H-pyrazol-4-yl]-6,7-dihydro-1H-purin-2-yl}-pyrrolidine-2-carboxylic acid;

1-{7-(2,2-Dimethyl-propionyloxymethyl)-6-oxo-1-propyl-8-[1-(3-trifluoromethyl-benzyl)-1H-pyrazol-4-yl]-6,7-dihydro-1H-purin-2-yl}-pyrrolidine-2-carboxylic acid;

2,2-Dimethyl-propionic acid 2-cyclopropyl-6-oxo-1-propyl-8-[1-(3-trifluoromethyl-benzyl)-1H-pyrazol-4-yl]-1,6-dihydro-purin-7-ylmethyl ester;

Phosphoric acid mono-{2-cyclopropyl-6-oxo-1-propyl-8-[1-(3-trifluoromethyl-benzyl)-1H-pyrazol-4-yl]-1,6-dihydro-purin-7-ylmethyl}ester;

Phosphoric acid mono-{2-chloro-6-oxo-1-propyl-8-[1-(6-trifluoromethyl-pyridin-3-ylmethyl)-1H-pyrazol-4-yl]-1,6-dihydro-purin-7-ylmethyl}ester;

Phosphoric acid mono-{6-oxo-1-propyl-8-[1-(6-trifluoromethyl-pyridin-3-ylmethyl)-1H-pyrazol-4-yl]-1,6-dihydro-purin-7-ylmethyl}ester;

Benzoic acid 2-cyano-6-oxo-1-propyl-8-[1-(3-trifluoromethyl-benzyl)-1H-pyrazol-4-yl]-1,6-dihydro-purin-7-ylmethyl ester;

7-Methoxymethyl-6-oxo-1-propyl-8-[1-(3-trifluoromethyl-benzyl)-1H-pyrazol-4-yl]-6,7-dihydro-1H-purine-2-carbonitrile;

Acetic acid 2-cyano-6-oxo-1-propyl-8-[1-(3-trifluoromethyl-benzyl)-1H-pyrazol-4-yl]-1,6-dihydro-purin-7-ylmethyl ester;

(S)-Pyrrolidine-1,2-dicarboxylic acid 1-benzyl ester 2-{2-cyano-6-oxo-1-propyl-8-[1-(3-trifluoromethyl-benzyl)-1H-pyrazol-4-yl]-1,6-dihydro-purin-7-ylmethyl}ester;

Butyric acid 2-cyano-6-oxo-1-propyl-8-[1-(3-trifluoromethyl-benzyl)-1H-pyrazol-4-yl]-1,6-dihydro-purin-9-ylmethyl ester;

Butyric acid 2-cyclopropyl-6-oxo-1-propyl-8-[1-(3-trifluoromethyl-benzyl)-1H-pyrazol-4-yl]-1,6-dihydro-purin-9-ylmethyl ester;

Butyric acid 2-chloro-6-oxo-1-propyl-8-[1-(3-trifluoromethyl-benzyl)-1H-pyrazol-4-yl]-1,6-dihydro-purin-9-ylmethyl ester;

Butyric acid 6-oxo-1-propyl-8-[1-(3-trifluoromethyl-benzyl)-1H-pyrazol-4-yl]-1,6-dihydro-purin-9-ylmethyl ester;

Phosphoric acid mono-{2-fluoro-6-oxo-1-propyl-8-[1-(3-trifluoromethyl-benzyl)-1H-pyrazol-4-yl]-1,6-dihydro-purin-9-ylmethyl}ester;

Phosphoric acid mono-{6-oxo-1-propyl-8-[1-(3-trifluoromethyl-benzyl)-1H-pyrazol-4-yl]-1,6-dihydro-purin-9-ylmethyl}ester; or Phosphoric acid mono-{2-cyclopropyl-6-oxo-1-propyl-8-[1-(3-trifluoromethyl-benzyl)-1H-pyrazol-4-yl]-1,6-dihydro-purin-9-ylmethyl}ester.

The compounds of Formula I and II are effective in-vivo for the treatment of conditions that respond to administration of $A_{2B}$ adenosine receptor antagonists. Such conditions include, but are not limited to, at least one of such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders including inflammatory bowel disease, sickle cell disease, neurodegenerative disorders and/or autoimmune diseases.

Pharmacokinetic Analysis

Compounds tested have shown good pharmacokinetic properties. Results have shown that compounds have ideal bioavailability profile of providing much higher plasma levels of the parent $A_{2B}$ adenosine receptor antagonist following oral dosing than is obtained by oral dosing of the parent compound itself.

Representative compounds showed that its peak serum concentration ($C_{max}$) is 200 μm as compared to 18 μm for the drug per se.

Hence, the plasma concentration of the representative compounds was found to be 5-10 fold.

Additionally, no trace of the prodrug were seen in plasma.

Although the subject matter has been described in considerable detail with reference to certain preferred embodiments thereof, other embodiments are possible. As such, the spirit and scope of the present disclosure should not be limited to the description of the preferred embodiment contained therein.

We claim:

1. A compound which is

Phosphoric acid mono-{2-cyano-6-oxo-1-propyl-8-[1-(3-trifluoromethyl-benzyl)-1H-pyrazol-4-yl]-1,6-dihydro-purin-7-ylmethyl}ester, Phosphoric acid mono-{2-cyano-6-oxo-1-propyl-8-[1-(3-trifluoromethyl-benzyl)-1H-pyrazol-4-yl]-1,6-dihydro-purin-9-ylmethyl}ester di sodium salt, Phosphoric acid mono-{2-chloro-6-oxo-1-propyl-8-[1-(3-trifluoromethyl-benzyl)-1H-pyrazol-4-yl]-1,6-dihydro-purin-7-ylmethyl}ester, Phosphoric acid mono-{2-chloro-6-oxo-1-propyl-8-[1-(3-trifluoromethyl-benzyl)-1H-pyrazol-4-yl]-1,6-dihydro-purin-9-ylmethyl}ester, 2,2-Dimethyl-propionic acid 6-oxo-1-propyl-8-[1-(3-trifluoromethyl-benzyl)-1H-pyrazol-4-yl]-1,6-dihydro-purin-7-ylmethyl ester, 2,2-Dimethyl-propionic acid 6-oxo-1-propyl-8-[1-(3-trifluoromethyl-benzyl)-1H-pyrazol-4-yl]-1,6-dihydro-purin-9-ylmethyl ester, 2,2-Dimethyl-propionic acid 2-chloro-6-oxo-1-propyl-8-[1-(3-trifluoromethyl-benzyl)-1H-pyrazol-4-yl]-1,6-dihydro-purin-7-ylmethyl ester, 7-Methoxymethyl-1-propyl-8-[1-(3-trifluoromethyl-benzyl)-1H-pyrazol-4-yl]-1,7-dihydro-purin-6-one, 9-Methoxymethyl-1-propyl-8-[1-(3-trifluoromethyl-benzyl)-1H-pyrazol-4-yl]-1,9-dihydro-purin-6-one, 2-Chloro-7-methoxymethyl-1-propyl-8-[1-(3-trifluoromethyl-benzyl)-1H-pyrazol-4-yl]-1,7-dihydro-purin-6-one, Phosphoric acid mono-{6-oxo-1-propyl-8-[1-(3-trifluoromethyl-benzyl)-1H-pyrazol-4-yl]-1,6-dihydro-purin-7-ylmethyl}ester, (2-Dimethylamino-ethyl)-methyl-carbamic acid 6-oxo-1-propyl-8-[1-(3-trifluoromethyl-benzyl)-1H-pyrazol-4-yl]-1,6-dihydro-purin-7-ylmethyl ester, (1-Ethyl-pyrrolidin-2-ylmethyl)-carbamic acid 6-oxo-1-propyl-8-[1-(3-trifluoromethyl-benzyl)-1H-pyrazol-4-yl]-1,6-dihydro-purin-7-ylmethyl ester, Nicotinic acid 6-oxo-1-propyl-8-[1-(3-trifluoromethyl-benzyl)-1H-pyrazol-4-yl]-1,6-dihydro-purin-7-ylmethyl ester, Acetic acid 6-oxo-1-propyl-8-[1-(3-trifluoromethyl-benzyl)-1H-pyrazol-4-yl]-1,6-dihydro-purin-7-ylmethyl ester, Butyric acid 6-oxo-1-propyl-8-[1-(3-trifluoromethyl-benzyl)-1H-pyrazol-4-yl]-1,6-dihydro-purin-7-ylmethyl ester, Butyric acid 2-chloro-6-oxo-1-propyl-8-[1-(3-trifluoromethyl-benzyl)-1H-pyrazol-4-yl]-1,6-dihydro-purin-7-ylmethyl ester, Nicotinic acid 2-chloro-6-oxo-1-propyl-8-[1-(3-trifluoromethyl-benzyl)-1H-pyrazol-4-yl]-1,6-dihydro-purin-7-ylmethyl ester, (2-Dimethylamino-ethyl)-methyl-carbamic acid 2-chloro-6-oxo-1-propyl-8-[1-(3-trifluoromethyl-benzyl)-1H-pyrazol-4-yl]-1,6-dihydro-purin-7-ylmethyl ester, (2-Dimethylamino-ethyl)-methyl-carbamic acid 2-cyano-6-oxo-1-propyl-8-[1-(3-trifluoromethyl-benzyl)-1H-pyrazol-4-yl]-1,6-dihydro-purin-7-ylmethyl ester, Butyric acid 2-cyano-6-oxo-1-propyl-8-[1-(3-trifluoromethyl-benzyl)-1H-pyrazol-4-yl]-1,6-dihydro-purin-7-ylmethyl ester, 2,2-Dimethyl-propionic acid 2-cyano-6-oxo-1-propyl-8-[1-(3-trifluoromethyl-benzyl)-1H-pyrazol-4-yl]-1,6-dihydro-purin-7-ylmethyl ester, Nicotinic acid 2-cyano-6-oxo-1-propyl-8-[1-(3-trifluoromethyl-benzyl)-1H-pyrazol-4-yl]-1,6-dihydro-purin-7-ylmethyl ester, 4-Methyl-piperazine-1-carboxylic acid 2-cyano-6-oxo-1-propyl-8-[1-(3-trifluoromethyl-benzyl)-1H-pyrazol-4-yl]-1,6-dihydro-purin-7-ylmethyl ester, 1-{6-Oxo-7-phosphonooxymethyl-1-propyl-8-[1-(3-trifluoromethyl-benzyl)-1H-pyrazol-4-yl]-6,7-dihydro-1H-purin-2-yl}-pyrrolidine-2-carboxylic acid, 1-{7-(2,2-Dimethyl-propionyloxymethyl)-6-oxo-1-propyl-8-[1-(3-trifluoromethyl-benzyl)-1H-pyrazol-4-yl]-6,7-dihydro-1H-purin-2-yl}-pyrrolidine-2-carboxylic acid, 2,2-Dimethyl-propionic acid 2-cyclopropyl-6-oxo-1-propyl-8-[1-(3-trifluoromethyl-benzyl)-1H-pyrazol-4-yl]-1,6-dihydro-purin-7-ylmethyl ester, Phosphoric acid mono-{2-cyclopropyl-6-oxo-1-propyl-8-[1-(3-trifluoromethyl-benzyl)-1H-pyrazol-4-yl]-1,6-dihydro-purin-7-ylmethyl}ester, Phosphoric acid mono-{2-chloro-6-oxo-1-propyl-8-[1-(6-trifluoromethyl-pyridin-3-ylmethyl)-1H-pyrazol-4-yl]-1,6-dihydro-purin-7-ylmethyl}ester, Phosphoric acid mono-{6-oxo-1-propyl-8-[1-(6-trifluoromethyl-pyridin-3-ylmethyl)-1H-pyrazol-4-yl]-1,6-dihydro-purin-7-ylmethyl}ester, Benzoic acid 2-cyano-6-oxo-1-propyl-8-[1-(3-trifluoromethyl-benzyl)-1H-pyrazol-4-yl]-1,6-dihydro-purin-7-ylmethyl ester, 7-Methoxymethyl-6-oxo-1-propyl-8-[1-(3-trifluoromethyl-benzyl)-1H-pyrazol-4-yl]-6,7-dihydro-1H-purine-2-carbonitrile, Acetic acid 2-cyano-6-oxo-1-propyl-8-[1-(3-trifluoromethyl-benzyl)-1H-pyrazol-4-yl]-1,6-dihydro-purin-7-ylmethyl ester, (S)-Pyrrolidine-1,2-dicarboxylic acid 1-benzyl ester 2-{2-cyano-6-oxo-1-propyl-8-[1-(3-trifluoromethyl-benzyl)-1H-pyrazol-4-yl]-1,6-dihydro-purin-7-ylmethyl}ester, Butyric acid 2-cyano-6-oxo-1-propyl-8-[1-(3-trifluoromethyl-benzyl)-1H-pyrazol-4-yl]-1,6-dihydro-purin-9-ylmethyl ester, Butyric acid 2-cyclopropyl-6-oxo-1-propyl-8-[1-(3-trifluoromethyl-benzyl)-1H-pyrazol-4-yl]-1,6-dihydro-purin-9-ylmethyl ester, Butyric acid 2-chloro-6-oxo-1-propyl-8-[1-(3-trifluoromethyl-benzyl)-1H-pyrazol-4-yl]-1,6-dihydro-purin-9-ylmethyl ester, Butyric acid 6-oxo-1-propyl-8-[1-(3-trifluoromethyl-benzyl)-1H-pyrazol-4-yl]-1,6-dihydro-purin-9-ylmethyl ester, Phosphoric acid mono-{2-fluoro-6-oxo-1-propyl-8-[1-(3-trifluoromethyl-benzyl)-1H-pyrazol-4-yl]-1,6-dihydro-purin-9-ylmethyl}ester, Phosphoric acid mono-{6-oxo-1-propyl-8-[1-(3-trifluoromethyl-benzyl)-1H-pyrazol-4-yl]-1,6-dihydro-purin-9-ylmethyl}ester, or Phosphoric acid mono-{2-cyclopropyl-6-oxo-1-propyl-8-[1-(3-trifluoromethyl-benzyl)-1H-pyrazol-4-yl]-1,6-dihydro-purin-9-ylmethyl}ester.

2. A pharmaceutical composition comprising, as an active ingredient, at least one compound as claimed in claim 1, or its stereoisomers or pharmaceutically acceptable salts thereof, together with one or more pharmaceutically acceptable carriers or excipients.

3. A pharmaceutical composition comprising, at least one compound as claimed in claim 1, or stereoisomers or a pharmaceutically acceptable salts thereof, in combination with one or more therapeutically active agents.

4. The pharmaceutical composition as claimed in claim 3 wherein, the therapeutically active agent is selected from anti-inflammatory agent, anti-diabetic agent, anti-hypertensive agent or anti-dyslipidemic agent.

5. The pharmaceutical composition as claimed in claim 3, wherein the one or more therapeutically active agent is selected from anticholinergic agent, antimuscarinic agent, steroid, LTB4 (leukotriene B4) antagonist, dopamine receptor agonists, phosphodiesterase 4 inhibitor, beta-2 adrenergic receptor agonist, insulin, insulin derivatives and mimetics, insulin secretagogues, insulinotropic sulfonylurea receptor ligands, thiazolidone derivatives, glycogen synthase kinase-3 inhibitor, sodium-dependent glucose co-transporter inhibitor, glycogen phosphorylase A inhibitor, biguanide, alpha-glucosidase inhibitor, glucagon like peptide-1 (GLP-1), GLP-1 analogs, GLP-1 mimetics, modulators of peroxisome proliferator-activated receptors, dipeptidyl peptidase IV inhibitor, stearoyl-CoA desaturase-1 inhibitor, diacylglycerol acyltransferase 1 and 2 inhibitor, acetyl CoA carboxylase 2 inhibitor, breakers of advanced glycation end products, loop diuretics, angiotensin converting enzyme inhibitor, inhibitor of the Na-K-ATPase membrane pump, neutralendopeptidase (NEP) inhibitor, ACE/NEP inhibitors, angiotensin II antagonists, renin inhibitors, β-adrenergic receptor blockers, inotropic agents, calcium channel blockers, aldosterone receptor antagonists, and aldosterone synthase inhibitors, 3-hydroxy-3-methyl-glutaryl coenzyme A reductase inhibitor, HDL increasing compounds, squalene synthase inhibitor, farnesoid X receptor and liver X receptor ligand, cholestyramine, fibrates, nicotinic acid, or aspirin.

* * * * *